United States Patent [19]

Quadri et al.

[11] Patent Number: 5,432,169
[45] Date of Patent: Jul. 11, 1995

[54] CYCLOPENTANPERHYDROPHENANTH- REN-17β-(3-FURYL)-3-DERIVATIVES AND PHARMACEUTICAL COMPOSITIONS COMPRISING SAME FOR THE TREATMENT OF CARDIOVASCULAR DISORDERS

[75] Inventors: Luisa Quadri, Cernusco; Luigi Bernardi, Milan; Patrizia Ferrari, Varese; Mauro Gobbini, Mercallo; Piero Melloni, Bresso; Loredana Valentino, Buccinasco, all of Italy

[73] Assignee: Sigma-Tau Industrie Farmaceutiche Riunite S.p.A., Rome, Italy

[21] Appl. No.: 81,111

[22] Filed: Jun. 25, 1993

[30] Foreign Application Priority Data

Jul. 1, 1992 [DE] Germany .................. 42 21 636.2

[51] Int. Cl.$^6$ ...................... C07J 17/00; A61K 31/58
[52] U.S. Cl. ...................... 514/172; 540/94; 540/114
[58] Field of Search .............. 540/94, 114; 514/172

[56] References Cited

U.S. PATENT DOCUMENTS 3,436,390 4/1969 Lefebrune et al. ............ 260/239.57
4,259,240 3/1981 Wiesner et al. ............ 260/239.55 R

FOREIGN PATENT DOCUMENTS 1807585 11/1968 Germany .
1812946 6/1970 Germany .
1081647 3/1966 United Kingdom .

OTHER PUBLICATIONS

Minato et al, Jour. Org. Chem pp. 377–379 (1966).
Humber et al, Steroids vol. 42 pp. 189–203 (1983).
Yoshii et al, Chem. Pharm. Bull vol. 24 3216–3219 (1976).
Steroids, Chapter 20 pp. 727–809 (1959).
Zürcher et al, Helvetica chimica Acta vol. 52 pp. 2449–2457 (1969).
Naidov et al, Jour of Pharmaceutical Science pp. 1391–1394 (1974).
Fritsch et al, Liebigr Ann. Chem vol. 727 pp. 110–120 (1969).
Templeton et al, J. Chem Soc pp. 251–256 (1983).
Vol. 88 et al, Gelvetica Chimica Acta vol. 16 pp. 108–116 (1959).

*Primary Examiner*—Nicholas Rizzo
*Attorney, Agent, or Firm*—Oblon, Spivak, McClelland, Maier & Neustadt

[57] ABSTRACT

Cyclopentanperhydrophenantren-17β-(3-furyl)-3-derivatives and pharmaceutical compositions containing same for the treatment of cardiovascular disorders such as heart failure and hypertension, are disclosed.

6 Claims, No Drawings

CYCLOPENTANPERHYDROPHENANTHREN-17β-(3-FURYL)-3-DERIVATIVES AND PHARMACEUTICAL COMPOSITIONS COMPRISING SAME FOR THE TREATMENT OF CARDIOVASCULAR DISORDERS

The present invention relates to cyclopentanperhydrophenanthren-17β-(3-furyl)-3-derivatives, a process for their preparation and pharmaceutical compositions containing same for the treatment of cardiovascular disorders such as heart failure and hypertension.

The compounds have formula (I):

wherein:

X is O or S;

the symbol ~ means that the substituents in positions 3, 5, 14, and 15 can have an α or β configuration, with the proviso that when X=S only the 3β configuration is present;

the symbol = means that single or double bonds can be present;

R is C2–C6 alkyl or C3–C5 alkenyl, substituted independently by a quaternary ammonium group or 2-(2-imidazolinyl) or one or more OR3, SR3, NR4R5, C(NH)NR6R7, with the proviso that when X is oxygen and R1 is [3OH and R2 is H and the configuration in position 5 is α and C2–C6 alkyl is ethyl or n-propyl, NR4R5 is not dimethylamino or morpholino;

R1 is H or hydroxy or methoxy or $O(CH_2)_n NR8R9$; wherein n is 2 or 3;

R2 is H or R1 and R2 taken together form an oxirane ring;

R3 is C2–C4 alkyl substituted by one or more NR6R7 or by NR6R7 and OH;

R4, R5 are independently H, methyl, C2–C6 alkyl or C3–C6 alkenyl unsubstituted or substituted by an oxirane or by one or more NR6R7, or NR6R7 and OH, or R4 and R5 taken together with the nitrogen atom form an unsubstituted or substituted, saturated or unsaturated penta- or hexa-monoheterocyclic ring optionally containing another heteroatom chosen from oxygen, sulphur or nitrogen, or R4 is hydrogen and R5 is C(NH)NH2;

R6, R7 are independently H, C1–C4 alkyl, or R6 and R7 taken together with the nitrogen atom form a saturated or unsaturated penta- or hexa-monoheterocyclic ring optionally containing another heteroatom chosen from oxygen, sulphur or nitrogen;

R8, R9 are independently H, methyl, ethyl or R8 and R9 taken together with the nitrogen atom form a saturated or unsaturated penta- or hexa-monoheterocyclic ring optionally containing another heteroatom chosen from oxygen, sulphur or nitrogen.

The invention includes within its scope all the possible stereoisomers, in particular Z and E isomers, optical isomers and their mixtures and the metabolites and the metabolic precursors of the compounds of formula (I).

Pharmaceutically acceptable salts of (I) are salts which retain the biologically activity of the base and are derived from such known acids pharmacologically acceptable such as e.g. hydrochloric, sulfuric, phosphoric, malic, tartaric, maleic, citric, methane-sulfonic or benzoic acid.

The alkyl and alkenyl groups may be branched or straight chain groups

The C2–C6 alkyl group is preferably a C2–C4 alkyl group, e.g. methyl, ethyl, propyl, isopropyl, butyl, sec-butyl.

The C3–C6 alkenyl group is preferably a C3–C4 alkenyl group.

The quaternary ammonium group is preferably a trimethylammonium- or a N-methylpyrrolidinium- or a N-methyl-piperidinium- group.

The OR3 group is preferably 2-aminoethoxy, 3-aminopropoxy, 2-dimethylaminoethoxy, 3-dimethylaminopropoxy, 3-amino-2-hydroxypropoxy, 2,3-diaminopropoxy, 2-(1-pyrrolidinyl)ethoxy, 3-(1-pyrrolidinyl)propoxy.

The SR3 group is preferably 2-aminoethylthio, 3-aminopropylthio, 2-dimethylaminoethylthio, 3-dimethylaminopropylthio, 3-amino-2-hydroxypropylthio, 2,3-diaminopropylthio, 2-(1-pyrrolidinyl)ethylthio, 3-(1-pyrrolidinyl)propylthio.

The NR4R5 group is preferably amino, methylamino, ethylamino, propylamino, isopropylamino, allylamino, propargylamino, dimethylamino, pyrrolidinyl, morpholino, piperazinyl, imidazolyl, guanidino, 2-aminoethylamino, 3-aminopropylamino, 2-(1-pyrrolidinyl)ethylamino, 3-(1-pyrrolidinyl)propylamino, 3-amino-2-hydroxypropylamino, 3-(1-pyrrolidinyl)2-hydroxypropylamino, 2,3-diaminopropylamino, (2-(1-pyrrolidinyl)ethyl)methylamino.

The C(NH)NR6R7 group is preferably a primary amidino group.

Preferred examples of specific compounds according to the present invention are:

3β-(2-Trimethylammonium-ethoxy)-17β-(3-furyl)-5β-androstan-14β-ol chloride

3β-(2-(N-Methyl-1-pyrrolydinium)ethoxy)-17β-(3-furyl)-5β-androstan-14β-ol iodide 3β-(2-Aminoethoxy)-17β-(3-furyl)-5β-androstan-14β-ol 3β-(3-Aminopropoxy)-17β-(3-furyl)-5β-androstan-14β-ol 3β-(4-Aminobutoxy)-17β-(3-furyl)-5β-androstan-14β-ol 3β-(4-Aminobut-(2-en)oxy)-17β-(3-furyl)-5β-androstan-14β-ol 3β-(4-Aminobut-(2-en)oxy)-17β-(3-furyl)-5β-androstan-14β-ol 3β-(2-Methylaminoethoxy)-17β-(3-furyl)-5β-androstan-14β-ol 3β-(2-(1-Pyrrolidinyl)ethoxy)-17β-(3-furyl)-5β-androstan-14β-ol 3β-(3-(1-Pyrrolidinyl)propoxy)-17β-(3-furyl)-5β-androstan-14β-ol 3β-(2-(1-Piperazinyl)ethoxy)-17β-(3-furyl)-5β-androstan-14β-ol 3β-(3-(1-Piperazinyl)propoxy)-17β-(3-furyl)-5β-androstan-14β-ol 3β-(2-(1-Imidazolyl)ethoxy)-17β-(3-furyl)-5β-androstan-14β-ol 3β-(2-(2-Imidazolin-2-yl)ethoxy)-17β-(3-furyl)-5β-androstan-14β-ol
3β-(2-(2-Amidino)ethoxy)-17β-(3-furyl)-5β-androstan-14β-ol
3β-(2-(2-Aminoethoxy)ethoxy)-17β-(3-furyl)-5β-androstan-14β-ol
3β-(2-(3-Aminopropoxy)ethoxy)-17β-(3-furyl)-5β-androstan-14β-ol
3β-(2-(2-(1-Pyrrolidinyl)ethoxy)ethoxy)-17β-(3-furyl)-5β-androstan-14β-ol.
3β-(2-(2-(1-Pyrrolidinyl)ethylthio)ethoxy)-17β-(3-furyl)-5β-androstan-14β-ol
3β-(2-(2-(1-Pyrrolidinyl)ethylamino)ethoxy)-17β-(3-furyl)-5β-androstan-14β-ol
3β-(2-(3-Dimethylaminopropoxy)ethoxy)-17β-(3-furyl)-5β-androstan-14β-ol
3β-(2-(3-Dimethylaminopropylthio)ethoxy)-17β-(3-furyl)-5β-androstan-14β-ol
3β-(2-(3-Dimethylaminopropylamino)ethoxy)-17β-(3-furyl)-5β-androstan-14β-ol
3β-(2-(3-(1-Pyrrolidinyl)propoxy)ethoxy)-17β-(3-furyl)-5β-androstan-14β-ol
3β-(2-(3-(1-Pyrrolidinyl)propylamino)ethoxy)-17β-(3-furyl)-5β-androstan-14β-ol
3β-(2-(3-Amino-2-hydroxypropoxy)ethoxy)-17β-(3-furyl)-5β-androstan-14β-ol
3β-(2-(2,3-Diaminopropoxy)ethoxy)-17β-(3-furyl)-5β-androstan-14β-ol
3β-(2,3-Bis(1-pyrrolidinyl)propoxy)-17β-(3-furyl)-5β-androstan-14β-ol
3β-(2-Guanidinoethoxy)-17β-(3-furyl)-5β-androstan-14β-ol
3β-(3-Guanidinopropoxy)-17β-(3-furyl)-5β-androstan-14β-ol
3β-(4-Guanidinobutoxy)-17β-(3β-furyl)-5β-androstan-14β-ol
3β-(2,3-Diaminopropoxy)-17β-(3-furyl)-5β-androstan-14β-ol
3β-(3-(3-Amino-2-hydroxypropoxy)propoxy)-17β-(3-furyl)-5β-androstan-14β-ol
3β-(3-(3-Amino-2-hydroxypropylamino)propoxy)-17β-(3-furyl)-5β-androstan-14β-ol
3β,14β-Bis(2-(1-pyrrolidinyl)ethoxy)-17β-(3-furyl)-5β-androstane
3β,14β-Bis(3-(1-pyrrolidinyl)propoxy)-17β-(3-furyl)-5β-androstane
3β-(3-Aminopropoxy)-14β-methoxy-17β-(3-furyl)-5β-androstane
3β-(2-(1-Pyrrolydinyl)ethoxy)-14β-methoxy-17β-(3-furyl)-5β-androstane
3β-(3-(1-Pyrrolidinyl)propoxy)-14β-methoxy-17β-(3-furyl)-5β-androstane
3β-(2-(2-(1-Pyrrolidinyl)ethoxy)ethoxy)-14β-methoxy-17β-(3-furyl)-5β-androstane
3β-(3-Aminopropoxy)-17β-(3-furyl)-androst-4-en-14β-ol
3β-(2-(1-Pyrrolidinyl)ethoxy)-17β-(3-furyl)-androst-4-en-14β-ol
3β-(3-(1 -Pyrrolidinyl)propoxy)-17β-(3-furyl)-androst-4-en-14β-ol
-(2-(2-(1-Pyrrolidinyl)ethoxy)ethoxy)-17β-(3-furyl)-androst-4-en-14β-ol
3β-(3-Aminopropoxy)-17β-(3-furyl)-androst-5-en-14β-ol
3β-(2-(1-Pyrrolidinyl)ethoxy)-17β-(3-furyl)-androst-5-en-14β-ol
3β-(3-(1-Pyrrolidinyl)propoxy)-17β-(3-furyl)-androst-5-en-14β-ol
3β-(2-(2-(1-Pyrrolidinyl)ethoxy)ethoxy)-17β-(3-furyl)-androst-5-en-14β-ol
3β-(3-Aminopropoxy)-17β-(3-furyl)-5α-androstan-14β-ol
3β-(2-(1-Pyrrolidinyl)ethoxy)-17β-(3-furyl)-5α-androstan-14β-ol
3β-(3-(1-Pyrrolidinyl)propoxy)-17β-(3-furyl)-5α-androstan-14β-ol
3β-(2-(2-(1-Pyrrolidinyl)ethoxy)ethoxy)-17β-(3-furyl)-5α-androstan-14β-ol
3β-(3-Aminopropoxy)-17β-(3-furyl)-5β-androstan-14α-ol
3β-(2-(1-Pyrrolidinyl)ethoxy)-17β-(3-furyl)-5β-androstan-14α-ol
3β-(3-(1-Pyrrolidinyl)propoxy)-17β-(3-furyl)-5β-androstan-14α-ol
3β-(2-(2-(1-Pyrrolidinyl)ethoxy)ethoxy)-17β-(3-furyl)-5β-androstan-14α-ol
3β-(3-Aminopropoxy)-14β,15β-epoxy-17β-(3-furyl)-5β-androstane
3β-(2-(1-Pyrrolidinyl)ethoxy)-14β,15β-epoxy-17β-(3-furyl)-5β-androstane
3β-(3-(1-Pyrrolidinyl)propoxy)-14β,15β-epoxy-17β-(3-furyl)-5β-androstane
3β-(2-(2-(1-Pyrrolidinyl)ethoxy)ethoxy)-14β,15β-epoxy-17β-(3-furyl)-5β-androstane
3β-(3-Aminopropoxy)-14β,15β-epoxy-17β-(3-furyl)-androst-4-ene
3β-(2-(1-Pyrrolidinyl)ethoxy)-14β,15β-epoxy-17β-(3-furyl)-androst-4-ene
3β-(3-(1-Pyrrolidinyl)propoxy)-14β,15β-epoxy-17β-(3-furyl)-androst-4-ene
3β-(2-(2-(1-Pyrrolidinyl)ethoxy)ethoxy)-14β,15β-epoxy-17β-(3-furyl)-androst-4-ene
3β-(3- Aminopropoxy)-14β,15β-epoxy-17β-(3-furyl)-androst-5-ene
3β-(2-(1-Pyrrolidinyl)ethoxy)-14β,15β-epoxy-17β-(3-furyl)-androst-5-ene
3β-(3-(1-Pyrrolidinyl)propoxy)-14β,15β-epoxy-17β-(3-furyl)-androst-5-ene
3β-(2-(2-(1-Pyrrolidinyl)ethoxy)ethoxy)-14β,15β-epoxy-17β-(3-furyl)-androst-5-ene
3β-(3-Aminopropoxy)-14β,15β-epoxy-17β-(3-furyl)-5α-androstane
3β-(2-(1-Pyrrolidinyl)ethoxy)-14β,15β-epoxy-17β-(3-furyl)-5α-androstane
3β-(3-(1-Pyrrolidinyl)propoxy)-14β,15β-epoxy-17β-(3-furyl)-5α-androstane
3β-(2-(2-(1-Pyrrolidinyl)ethoxy)ethoxy)-14β,15β-epoxy-17β-(3-furyl)-5α-androstane
3β-(3-Aminopropoxy)-14α,15α-epoxy-17β-(3-furyl)-5β-androstane
3β-(2-(1-Pyrrolidinyl)ethoxy)-14α,15α-epoxy-17β-(3-furyl)-5β-androstane
3β-(3-(1-Pyrrolidinyl)propoxy)-14α,15α-epoxy-17β-(3-furyl)-5β-androstane
3β-(2-(2-(1-Pyrrolidinyl)ethoxy)ethoxy)-14α,15α-epoxy-17β-(3-furyl)-5β- androstane
3β-(3-Aminopropoxy)-17β-(3-furyl)-5β,14β-androstane
3β-(2-(1-Pyrrolidinyl)ethoxy)-17β-(3-furyl)-5β,14β-androstane
3β-(3-(1-Pyrrolidinyl)propoxy)-17β-(3-furyl)-5β,14β-androstane
3β-(2-(2-(1-Pyrrolidinyl)ethoxy)ethoxy)-17β-(3-furyl)-5β,14β-androstane
3β-(3-Aminopropoxy)-17β-(3-furyl)-androst-4-ene 3β-(2-(1-Pyrrolidinyl)ethoxy)-17β-(3-furyl)-androst-4-ene 3β-(3-(1-Pyrrolidinyl)propoxy)-17β-(3-furyl)-androst-4-ene 3β-(2-(2-(1-Pyrrolidinyl)ethoxy)ethoxy)-17β-(3-furyl)-androst-4-ene 3β-(3-Aminopropoxy)-17β-(3-furyl)-androst-5-ene 3β-(2-(1-Pyrrolidinyl)ethoxy)-17β-(3-furyl)-androst-5-ene 3β-(3-(1-Pyrrolidinyl)propoxy)-17β-(3-furyl)-androst-5-ene 3β-(2-(2-(1-Pyrrolidinyl)ethoxy)ethoxy)-17β-(3-furyl)-androst-5-ene 3β-(3-Aminopropoxy)-17β-(3-furyl)-5α-androstane 3β-(2-(1-Pyrrolidinyl)ethoxy)-17β-(3-furyl)-5α-androstane 3β-(3-(1-Pyrrolidinyl)propoxy)-17β-(3-furyl)-5α-androstane 3-(2-(2-(1-Pyrrolidinyl)ethoxy)ethoxy)-17β-(3-furyl)-5α-androstane 3-(3-Aminopropoxy)-17β-(3-furyl)-5β-androstane 3-(2-(1-Pyrrolidinyl)ethoxy)-17β-(3-furyl)-5β-androstane 3β-(3-(1-Pyrrolidinyl)propoxy)-17β-(3-furyl)-5β-androstane 3β-(2-(2-(1-Pyrrolidinyl)ethoxy)ethoxy)-17β-(3-furyl)-5β-androstane 3-(2-(4-Morpholinoethylthio)-17β-(3-furyl)-5β-androstan-14β-ol and the corresponding X=S derivatives and for X=O the corresponding 3α derivatives.

The starting materials for preparing the compounds of formula (I), wherein X=O, R1 and R2 are as above defined, are compounds of formula (II), wherein X=O, R1 is hydrogen or hydroxy and R2 is H, or R1 and R2 taken together form an oxirane ring, which are known compounds such as, for example, 17β-(3-furyl)-5α-androstan-3β-ol, 17β-(3-furyl)-5β-androstan-3β-ol (U.S. Pat. No. 3,436,390), 17β-(3-furyl)-5β-androstane-3β,14β-diol (Minato H. and Nagasaki T., J. Chem. Soc.(C), 1966, 377), 17β-(3-furyl)-5β-androstane-3α,14β-diol (Humber D. et al., Steroids, 1983, 42,189), 14β,15β-epoxy-17β-(3-furyl)-5β-androstan-3β-ol (Yoshii E. et al., Chem. Pharm. Bull., 1976, 24, 3216) or are prepared from the known compounds with methods well known to those skilled in the art.

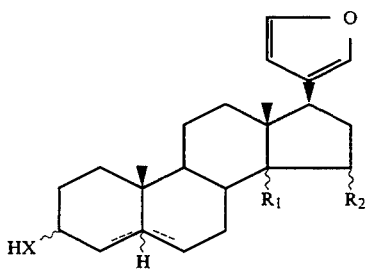

(II)

For instance, the compounds of formula (II), wherein X=O, R1 is hydrogen or hydroxy, R2 is H or R1 and R2 taken together form an oxirane ring, can be obtained from known 3-oxo derivatives (III), wherein R1 is hydrogen or hydroxy, R2 is H or R1 and R2 taken together form an oxirane ring, such as, e.g. 14β-hydroxy-17β-(3-furyl)-androst-4-en-3-one (GB. Pat. 1081647), 17β-(3-furyl)-androst-4-en-3-one, 17β-(3-furyl)-5α-androstan-3-one (U.S. Pat. No. 3436390), by reduction with complex hydrides, e.g. NaBH4 or LiAlH4 or tri-tert-butoxyaluminum-hydride, the 3α or 3β isomer depending on the reducing reagent.

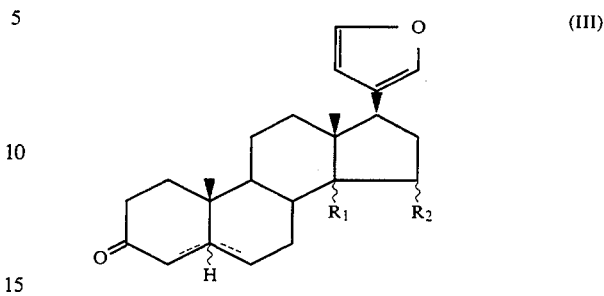

(III)

Alternatively, the compounds of formula (II), wherein X=O, R1 is H or hydroxy, R2 is H or R1 and R2 taken together form an oxirane ring, can be obtained from known 17β-lactones of 3α or 3β hydroxy derivatives (IV), wherein R1 is H or hydroxy, R2 is H or R1 and R2 taken together form an oxirane ring, such as, e.g. canarigenin, xysmalogenin, uzarigenin (Fieser L. F. and Fieser M. in "Steroids", 1959, pp. 727–809; Minato H. and Nagasaki T., J. Chem. Soc. (C), 1966, 377), 3β-hydroxy-14α-hydroxy-5β-card-20(22)-enolide (Zurcher W. et al., Helv. Chim. Acta, 1969, 52, 2449), 3β-hydroxy-5β,14β-card-20(22)-enolide (Naidoo K., J. Pharm. Science., 1974, 23, 1391), 3β-hydroxy-14β,15β-epoxy-carda-4,20(22)-dienolide (Fritsch W. et al., Ann. Chem., 1969, 727, 110), 3β-acetoxy-14β,15β-epoxy-carda-5,20(22)-dienolide (Yoshii E., Ozaki K., Chem. Pharm. Bull., 1972, 20, 1585), 3β-hydroxy-14β,15β-epoxy-5α-card-20(22)-enolide (DE Pat. 1807585), 3β-hydroxy-14α,15α-epoxy-card-20(22)-enolide (Ishii H, Chem. Pharm. Bull., 1963, 11, 576), by reduction with complex hydrides, e.g. diisobutylaluminum-hydride;

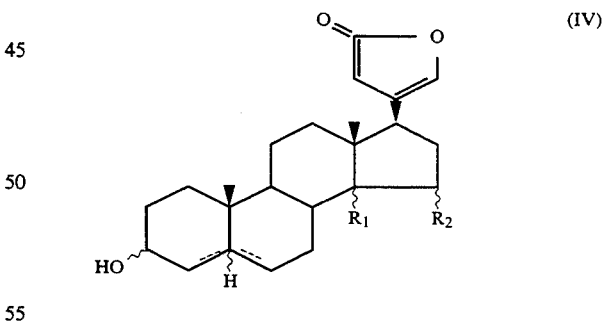

(IV)

or are obtained from known 3-oxo and 17β-lactones (V), wherein R1 is hydroxy, R2 is H or R1 and R2 taken together form an oxirane ring, such as, e.g. 3-oxo-14β-hydroxy-5α-card-20(22)-enolide (Templeton, J. F. et al., J. Chem. Soc., Perkin Trans. 1, 1983, 251), 3-oxo-14β-hydroxy-carda-5,20(22)-dienolide (Volpp G., and Tamm C., Helv. Chim. Acta, (42), 1959, 1408), 3-oxo-14β,15β-epoxy-carda-4,20(22)-dienolide (DE Pat. 1812946), 3-oxo-14β,15β-epoxy-5α-card-20(22)-enolide (DE Pat. 1807585), by reduction with complex hydrides, e.g. diisobutylaluminum-hydride.

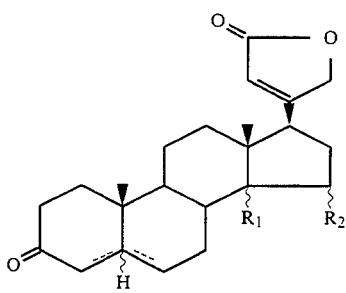

Finally, they can be obtained from 3β-hydroxy-androst-5-en-17-one, as described in the experimental section, following known methods.

Compounds of formula (II), wherein X=O, R1 is different from hydrogen or hydroxy and R2 is hydrogen are obtained from the corresponding compounds wherein R1 is hydroxy, by treatment with methyl iodide or with a compound of formula (VI)

wherein Y is an electron-withdrawing group, such as e.g. halogen, mesyloxy, or tosyloxy group, which confers electrophilic properties to the attached carbon atom and n, R8 and R9 are as above defined: the hydroxy group present in position 3 is protected with methods well known to those skilled in the art, to give after removal of protective group the compounds of general formula (II).

The compounds (II) wherein X=S, R1 and R2 are as above defined, are novel compounds and are obtained by ammonolysis of the acetylthio derivatives (VII), wherein R1 and R2 are as above defined,

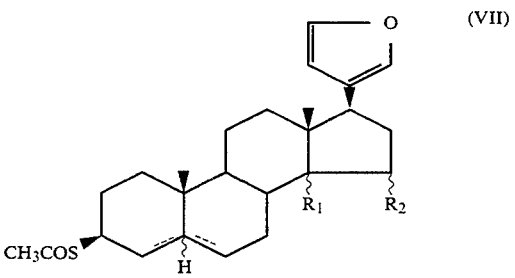

which in turn are obtained by reaction of the corresponding 3α-hydroxy derivatives (II) with thiolacetic acid in the presence of a dialkyl azodicarboxylate and triphenylphosphine.

The invention furthermore provides a process for the preparation of said compounds (I), which comprises the condensation of compounds having formula (II), wherein X, R1 and R2 are as above defined, with a compound of formula (VIII)

wherein Y is an electron-withdrawing group, such as halogen, mesyloxy, or tosyloxy group, which confers electrophilic properties to the attached carbon atom, and R is as above defined, the free hydroxy and amino groups, if any, present in R being protected, if necessary, with methods well known to those skilled in the art to give, after removal of the protective groups, if any, compounds of general formula (I) which may be converted into other compounds of formula (I) and optionally converting compounds (I) into pharmaceutically acceptable salts thereof and optionally separating a mixture of isomers into single isomers.

The condensation reaction between (II) and (VIII) is best carried out in an inert aprotic solvent, such as tetrahydrofuran, dioxane, dimethylformamide, dimethylsulfoxyde or in the neat (VII) and in the presence of a strong base e.g. sodium or potassium hydride at a temperature ranging from 10° C. to about 110 ° C.

The purification is best performed by flash-chromatography on silica gel.

Examples of conversion of compounds of general formula (I) into other compounds of formula (I) are the following.

Compounds (I) wherein a C(=NH)NH$_2$ or a 2-imidazolinyl group are present can be obtained by reacting the corresponding compounds of formula (I)-wherein a CN group is present with e.g. methylchloroaluminum amide or 1,2-diaminoethane in the presence of hydrogen sulfide.

Compounds (I) wherein a guanidino group is present can be obtained by reacting the corresponding compounds of formula (I) wherein a primary amine is present with e.g. 1-amidino-3,5-dimethylpyrazole nitrate. All said transformations are only examples of well established procedures described in Organic Chemistry (see for example: J. March "Advanced Organic Chemistry", J. Wiley & Sons, 1985; D. Barton and W. D. Ollis "Comprehensive Organic Chemistry", Pergamon Press, 1979) well known to those skilled in the art.

The compounds of general formula (VI) and (VIII) are known compounds, generally commercially available or preparable from known compounds by known methods.

The derivatives (I), prepared according to the invention and their pharmaceutically acceptable salts have much reduced toxicity compared to the known 17β-(3-furyl)-5β-androstane-3β,14β-diol (II-a: Ref. comp.) (Minato H. and Nagasaki T., J. Chem. Soc.(C), 1966, 377) and are useful agents for the treatment of cardiovascular disorders such as heart failure and hypertension. Moreover said compounds (I) show higher affinity for the receptor site of the Na$^+$, K$^+$-ATPase than (II-a) and behave as partial agonists on the enzymatic activity of the Na$^+$,K$^+$-ATPase.

To test the affinity for the receptor site of the Na$^+$,K$^+$-ATPase and the agonist or antagonist activity on the enzyme, the following tests were used: a) displacement of the specific $^3$H-ouabain binding from the Na$^+$,K$^+$-ATPase receptor purified according to Jorghensen (Jorghensen P., BBA, 1974, 356, 36) and Erdmann ( Erdmann E. et al., Arzneim. Forsh., 1984, 34, 1314); b) inhibition of the activity of the purified Na$^+$,K$^+$-ATPase measured as % of hydrolysis of $^{32}$P-ATP in presence and in absence of the tested compound (Mall F. et al., Biochem. Pharmacol., 1984, 33, 47).

The ability of these compounds to lower blood pressure in adult hypertensive MHS rats was tested by the following method: systolic blood pressure (SBP) and heart rate (HR) were measured by an indirect tail-cuff method in three-month old hypertensive MHS rats before beginning treatment (basal values). The rats were then subdivided in two groups of 7 animals each, one receiving the compound and the other, the control group, receiving only the vehicle. The compound, suspended in METHOCEL ®0.5% (w/v), for ten days, was administered daily by mouth. SBP and HR were measured daily 6 and 24 hours after the treatment. When ten-day treatment washout had been under way for at least two days, whether the treatment mantains SBP low or re-establish the basal values was verified.

The affinity and the inhibitory activity of some ethers and of the reference compound (II-a) in the two tests are shown in the following table:

|  | Binding $^3$H-Ouab. Displacement -log IC50 | Inhibitory Activity -log IC50 |
| --- | --- | --- |
| Comp. I - aa | 6.8 | 6.3 |
| Comp. I - ab | 6.9 | 5.9 |
| Comp. I - ac | 6.4 | 5.7 |
| Comp. I - ad | 6.8 | 6.0 |
| Comp. I - ae | 6.9 | 6.1 |
| Comp. I - af | 7.0 | 5.9 |
| Comp. I - ag | 6.8 | 5.8 |
| Comp. I - ah | 6.8 | 6.1 |
| Comp. I - ai | 6.7 | 6.2 |
| Comp. I - aj | 6.8 | 5.9 |
| Comp. I - ak | 6.8 | 5.9 |
| Comp. I - al | 6.9 | 5.8 |
| Comp. I - am | 6.7 | 5.5 |
| Comp. I - an | 6.7 | 5.8 |
| Comp. I - ao | 6.5 | 5.8 |
| Comp. I - ap | 6.4 | 5.8 |
| Comp. I - ar | 5.5 | 4.6 |
| Comp. I - as | 5.3 | 4.6 |
| Comp. I - at | 6.2 | 5.6 |
| Comp. I - au | 6.5 | 5.8 |
| Comp. I - av | 6.2 | 5.6 |
| Comp. I - aw | 5.8 | 5.2 |
| Comp. I - ay | 6.4 | 5.5 |
| Comp. I - ba | 6.2 | 5.8 |
| Comp. I - bc | 6.5 | 5.7 |
| Comp. I - bu | 6.5 | 6.2 |
| Comp. I - bv | 6.3 | 5.7 |
| Comp. I - bw | 6.1 | 5.4 |
| Comp. I - bx | 6.3 | 6.0 |
| Comp. I - by | 6.8 | 6.0 |
| Comp. I - ce | 6.0 | 5.5 |
| Comp. I - cj | 5.7 | 5.2 |
| Comp. I - cx | 6.7 | 5.8 |
| Comp. I - cy | 6.4 | 5.8 |
| Comp. I - cz | 6.4 | 5.7 |
| Comp. I - da | 6.5 | 5.8 |
| Comp. I - db | 6.7 | 5.8 |
| Comp. II - a | 6.3 | 5.7 |

The activity of the Ref. compound II-a and some basic ethers in preventing the development of hypertension is shown in the following table:

| SYSTOLIC BLOOD PRESSURE FALL IN SPONTANEOUS HYPERTENSIVE RATS (MHS) | | | | |
| --- | --- | --- | --- | --- |
| COMPOUNDS | RATS | DOSE* mg/Kg/os | SBP mm Hg | HR beats/min. |
| Controls | 7 | METHOCEL ® | 171 ± 4.5 | 384 ± 11.0 |
| Comp. I-ab | 7 | 20 | 157 ± 4.9 | 371 ± 10.0 |
| Comp. I-ae | 7 | 20 | 154 ± 6.3 | 395 ± 8.7 |
| Comp. I-ag | 7 | 20 | 162 ± 5.0 | 377 ± 9.0 |
| Comp. I-ai | 7 | 20 | 160 ± 4.7 | 390 ± 8.9 |
| Comp. I-al | 7 | 20 | 159 ± 5.0 | 393 ± 9.0 |
| Comp. I-bv | 7 | 20 | 161 ± 4.2 | 384 ± 6.7 |
| Comp. I-bw | 7 | 20 | 157 ± 4.3 | 392 ± 10.0 |
| Comp. I-by | 7 | 20 | 154 ± 6.3 | 395 ± 8.7 |
| Comp. II-a | 7 | 20 | 175 ± 4.1 | 382 ± 9.0 |

*in METHOCEL ® 0.5% w/v

The following examples illustrate the invention without limiting it.

EXAMPLE 1

3$\beta$-(2- Aminoethoxy)-17$\beta$-(3-furyl)-5$\beta$-androstan-14$\beta$-ol (I-aa)

To a suspension of 5.5 g of NaH (60% dispersion in mineral oil) in 400 ml of dry tetrahydrofuran 7.0 g of 17$\beta$)-(3-furyl)-5$\beta$-androstane-3$\beta$,14$\beta$-diol (II-a: Ref, comp.) (Minato H. and Nagasaki T., J. Chem. Soc.(C), 1966, 377) were added at room temperature in a nitrogen atmosphere. The mixture was kept at reflux for 6 hrs, then 26 ml of bromoacetaldehyde diethylacetal were added; the suspension was kept at reflux temperature for 4 hrs, 50 ml of water were added cautiously, and the tetrahydrofuran was distilled under reduced pressure. The residue was extracted with methylene chloride, the organic layer was dried over anhydrous sodium sulfate and evaporated to dryness under reduced pressure. The crude product was purified by flash-chromatography (SiO$_2$) using n-hexane/ethyl acetate 80/20 as eluant to give 6.9 g of 3$\beta$-(2,2-diethoxy-ethoxy)-17$\beta$-(3-furyl)-5$\beta$-androstan-14$\beta$-ol, as a dense oil.

$^1$H NMR (300 MHz, CDCl$_3$, ppm from TMS): 0.72 (3H, s); 0.93 (3H, s); 1.22 (6H, t); 2.74 (1H, dd); 3.47–3.50 (2H, m); 3.50–3.80 (5H, m); 4.62 (1H, t); 6.46 (1H, bs); 7.20 (1H, bs); 7.30 (1H, bs).

A solution of 3.8 g of 3$\beta$-(2,2-diethoxy-ethoxy)-17$\beta$-(3-furyl)-5$\beta$-androstan-14$\beta$-ol, in 300 ml of dioxane and 230 ml of a saturated solution of tartaric acid was heated at 70° C. for two hrs in a nitrogen atmosphere, 100 ml of water were then added and the residue was extracted with methylene chloride. The organic layer was washed with water., dried over anhydrous sodium sulfate and evaporated to dryness under reduced pressure. The crude product was purified by flash-chromatography (SiO$_2$) using as eluant n-hexane/ethyl acetate 70/30 to give 2.0 g of 3-$\beta$-formylmethoxy-17$\beta$-(3-furyl)-5$\beta$-androstan-14$\beta$-ol as a white solid.

$^1$H NMR: (300 MHz, CDCl$_3$, ppm from TMS): 0.75 (3H, s); 0.95 (3H, s); 2.74 (1H, dd); 3.70 (1H, bs); 4.10 (2H, d); 6.48 (1H, bs); 7.20 (1H, bs); 7.32 (1H, bs); 9.78 (1H, t).

To a solution of 2.0 g of 3-$\beta$-formylmethoxy-17$\beta$-(3-furyl)-5$\beta$-androstan-14$\beta$-ol in 100 ml of methanol, 0.30 g of sodium borohydride were added slowly at 0° C. After half an hr the temperature of the mixture was left to rise to 25° C. After 2 hrs 20 ml of water were added, the methanol was distilled under reduced pressure, and the mixture was extracted with methylene chloride; the organic layer was washed with water, dried over sodium sulfate and evaporated to dryness under reduced pressure. The crude product was purified by flash-chromatography (SiO$_2$) using n-hexane/ethyl acetate 80/20 as eluant to give 1.8 g of 3β-(2-hydroxyethoxy)-17β-(3-furyl)-5β-androstan-14β-ol as a white solid.

$^1$H NMR (300 MHz, CDCl$_3$, ppm from TMS): 0.70 (3H, s); 0.90 (3H, s); 2.72 (1H, dd); 3.147 (2H, t); 3.63 (1H, bs); 3.70 (2H, t); 6.44 (1H, bs); 7.18 (1H, bs); 7.30 (1H, bs).

A solution of 0.29 ml of diethyl azodicarboxylate was added dropwise, under nitrogen, to a solution of 0.75 g of 3β-(2-hydroxyethoxy)-17β-(3-furyl)-5β-androstan-14β-ol, 0.28 g of phthalimide and 0.50 g of triphenylphosphine in 7 ml of tetrahydrofuran at room temperature. After 2 hrs the solvent was removed in vacuo, the crude product was dried over anhydrous sodium sulfate and evaporated to dryness under reduced pressure. The crude product was purified by flash-chromatography (SiO$_2$) using n-hexane/ethyl acetate 80/20 to give 0.70 g of 3β-(2-phthalimidoethoxy)-17β-(3-furyl)-5β-androstan-14β-ol.

$^1$H NMR (300 MHz, CDCl$_3$, ppm from TMS): 0.68 (3H, s); 0.70 (3H, s); 2.72 (1H, dd); 3.60–3.68 (3H, m); 3.87–3.95 (2H, m); 6.43 (1H, bs); 7.20 (1H, bs); 7.30 (1H, bs); 7.70–7.76 (2H, m); 7.83–7.92 (2H, m).

To a solution of 0.50 g of 3β-(2-phthalimidoethoxy)-17β-(3-furyl)-5β-androstan-14β-ol in 50 ml of ethanol (96%) 0.19 g of hydrazine hydrate were added at room temperature. The mixture was kept at reflux for 4 hrs, then 10 ml of water were added and the ethanol distilled under reduced pressure. The residue was extracted with methylene chloride, the organic solution was washed with water, dried over anhydrous sodium sulfate and evaporated to dryness under reduced pressure. The crude residue was purified by flash-chromatography (SiO$_2$) using methylene chloride/methanol 90/10 as eluant to give 0.35 g of the title compound (I-aa) as a white solid.

$^1$H NMR: (300 MHz, CDCl$_3$, ppm from TMS): 0.70 (3H, s); 0.92 (3H, s); 2.74 (1H, dd); 2.84 (2H, t); 3.41 (2H, m); 3.65 (1H, bs); 6.48 (1H, bs); 7.20 (1H, bs); 7.32 (1H, bs).

EXAMPLE 2

3β-(3-Aminopropoxy)-17β-(3-furyl)-5β-androstan-14β-ol (I-ab)

To a solution of 0.60 g of 17β-(3-furyl)-5β-androstane-3β,14β-diol (II-a: Ref. comp.) (Minato H. and Nagasaki T., *J. Chem. Soc.* (C), 1966, 377) in 50 ml of dry tetrahydrofuran, 0.44 g of sodium hydride (60% dispersion in mineral oil) were added under nitrogen atmosphere at room temperature and the resulting mixture was stirred at reflux temperature for 6 hrs; 1.4 g of allyl bromide were added and the reflux continued for further 20 hrs. The mixture was quenched with water and the organic solvent was distilled under reduced pressure. The residue was extracted with ethyl acetate, the organic solution was dried over anhydrous sodium sulfate and evaporated to dryness under reduced pressure. The residue was purified by flash-chromatography (SiO$_2$) using n-hexane/ethyl acetate 80/20 as eluant to give 0.58 g of 3β-(prop-2-enoxy)-17β-(3-furyl)-5β-androstan-14β-ol as a white solid.

$^1$H-NMR (300 MHz, CDCl$_3$, ppm from TMS): 0.72 (3H, s); 0.92 (3H, s); 2.74 (1H, dd); 3.68 (1H, bs); 3.9–4 (2H, m); 5.12–5.18 (1H, m); 5.22–5.33 (1H, m); 5.87–6.01 (1H, m); 6.47 (1H, bs); 7.21 (1H, bs); 7.32 (1H, bs).

To a solution of 0.17 g of 9-borabicyclo[3.3.1]nonane in 35 ml of dry tetrahydrofuran, 0.50 g of 3β-(prop-2-enoxy)-17β-(3-furyl)-5-androstan-14β-ol in 10 ml of tetrahydrofuran were added under nitrogen atmosphere, at room temperature. The solution was stirred for 6 hrs then 0.75 ml of ethanol, 0.25 ml of sodium hydroxide 6 N and 0.50 ml of hydrogen peroxide 30% were added. The mixture was stirred at 50° C. for an hr, quenched with a solution of 0.76 g of potassium carbonate in 20 ml of water and the organic solvent distilled under reduced pressure. The residue was extracted with methylene chloride, the organic solution was dried over anhydrous sodium sulfate and evaporated to dryness under reduced pressure. The residue was purified by flash-chromatography (SiO$_2$) using n-hexane/ethyl acetate 70/30 as eluant to give 0.40 g of 3β-(3-hydroxypropoxy)-17β-(3-furyl)-5β-androstan-14β-ol as a white amorphous solid.

$^1$H-NMR (300 MHz, CDCl$_3$, ppm from TMS): 0.70 (3H, s); 0.94 (3H, s); 2.74 (1H, dd); 3.57–3.67 (3H, m); 3.78–3.83 (2H, m); 6.48 (bs,1H); 7.21 (1H, bs); 7.31 (1H, bs).

0.15 g of 3β-(3-hydroxypropoxy)-17β-(3-furyl)-5β-androstan-14β-ol were first changed into the phtalimido derivative 3β-(3-phthalimidopropoxy)-17β-(3-furyl)-5β-androstan-14β-ol and then in 0.11 g of the title compound (I-ab) as a white solid, using the same procedure described in Ex. 1.

$^1$H NMR: (300 MHz, CDCl$_3$, ppm from TMS): 0.70 (3H, s); 0.91 (3H, s); 2.60–2.80 (3H, m); 3.30–3.40 (2H, m); 3.57 (1H, bs); 6.45 (1H, bs); 7.20 (1H, bs); 7.31 (1H, bs).

EXAMPLE 3

3β-(4-Aminobutoxy)-17β-(3-furyl)-5β-androstan-14β-ol (I-ac)

To a stirred suspension of 0.50 g of anhydrous lithium chloride in 120 ml of anhydrous acetonitrile, 2.7 g of triethyl phosphonoacetate, 1.5 g of 1,8-diazabicyclo[5.4.0]undec-7-ene and 4.0 g of 3β-formylmethoxy-17β-(3-furyl)-5β-androstan-14β-ol, prepared as intermediate in Ex.1, were added under nitrogen at room temperature. After an hr, 50 ml of water were added and the organic solvent distilled under reduced pressure. The residue was extracted with methylene chloride, the organic layer was dried over anhydrous sodium sulfate and evaporated :to dryness under reduced pressure; the crude product was purified by flash-chromatography (SiO$_2$), using as eluant n-hexane/ethyl acetate 80/20 to give 4.3 g of 3β-(3-carbethoxyprop-2-enoxy)-17β-(3-furyl)-5β-androstan-14β-ol as a white amorphous solid.

$^1$H NMR: (300 MHz, CDCl$_3$, ppm from TMS): 0.72 (3H, s); 0.93 (3H, s); 2.74 (1H, dd); 3.68 (1H, bs); 4.00–4.30 (4H, m); 6.10–6.30 (1H, m); 6.44 (1 H, bs); 7.00–7.35 (3 H, m)

To a solution of 0.40 g of 3β-(3-carbethoxyprop-2-enoxy)-17β-(3-furyl)-5β-androstan-14β-ol in 30 ml of anhydrous tetrahydrofuran, 2 ml of sodium bis(2-methoxyethoxy)aluminum hydride (solution 3.4 M in toluene) were added at room temperature. The solution was kept at reflux temperature for 8 hrs, then 10 ml of water were added and the organic solution was evaporated to dryness under reduced pressure. The residue was extracted with ethyl acetate and the organic layer was dried over anhydrous sodium sulfate and evaporated to dryness under reduced pressure. The crude product was purified by flash-chromatography using n-hexane/ethyl acetate 70/30 as eluant to give 0.30 g of 3β-(4-hydroxybutoxy)-17β-(3-furyl)-5β-androstan-14β-ol, as a white pasty solid.

¹H NMR: (300MHz, CDCl₃, ppm from TMS): 0.70 (3H, s); 0.90 (3H, s); 2.74 (1H, dd); 3.45–3.65 (3H, m); 3.70–3.90 (2H, m); 6.44 (1H, bs); 7.18 (1H, bs); 7.30 (1H, bs).

0.90 g of 3β-(4-hydroxybutoxy)-17β-(3-furyl)-5β-androstan-14β-ol were first changed into the phtalimido derivative 3β-(4-phthalimidobutoxy)-17β-(3-furyl)-5β-androstan-14β-ol and then in 0.85 g of the title compound (I-ac) as a white solid, using the same procedure described in Ex. 1.

¹H NMR: (300 MHz, CDCl₃, ppm from TMS): 0.70 (3H, s); 0.90 (3H, s); 2.70–2.80 (3H, m); 3.32–3.43 (2H, m); 3.57 (1H, bs); 6.45 (1H, bs); 7.20 (1H, bs); 7.31 (1H, bs).

EXAMPLE 4

3β-(2-(1-Pyrrolydinyl)ethoxy)-17β-(3-furyl)-5β-androstan-14β-ol (I-ad)

To a suspension of 0.80 g of NaH (60% dispersion in mineral oil) in 85 ml of dry tetrahydrofuran 1.0 g of 17β-(3-furyl)-5β-androstane-3β,14β-diol (II-a: Ref. comp.) (Minato H. and Nagasaki T., *J. Chem. Soc.* (C), 1966, 377) were added at room temperature under nitrogen atmosphere. The mixture was kept at reflux for 6 hrs, then 3.2 g of 1-(2-chloroethyl)pyrrolidine were added; the suspension was refluxed for 4 hrs, 50 ml of water were added cautiously and the tetrahydrofuran was distilled at reduced pressure. The residue was extracted with methylene chloride, the organic layer was dried over anhydrous sodium sulfate and evaporated to dryness under reduced pressure. The crude product was purified by flash-chromatography (SiO₂) using methylene chloride/methanol 70/30 as eluant to give 0.91 g of the title compound (I-ad), as a white solid.

¹H-NMR (300 MHz, CDCl₃, ppm from TMS): 0.70 (3H, s); 0.91 (3H, s); 2.50–2.62 (4H, m); 2.64–2.80 (3H, m); 3.48–3.58 (2H, m); 3.62 (1H, bs); 6.45 (1H, bs); 7.20 (1H, bs); 7.30 (1H, bs).

EXAMPLE 5

3β-(3-(1-Pyrrolydinyl)propoxy)-17β-(3-furyl)-5β-androstan-14β-14β(I-ae)

The title compound (I-ae) (0.65 g) was obtained as a white solid from 17β-(3-furyl)-5β-androstane-3β,14β-diol (II-a: Ref. comp.) (Minato H. and Nagasaki T., *J. Chem. Soc.* (C), 1966, 377) (0.60 g) using the same procedure described in Ex. 4.

¹H-NMR (300 MHz, CDCl₃, ppm :from TMS): 0.72 (3H, s); 0.92 (3H, s); 2.46–2.52 (6H, m); 2.74 (1H, dd); 3.42 (2H, t); 3.61 (1H, bs); 6.46 (1H, bs); 7.20 (1H, bs); 7.30 (1H, bs).

EXAMPLE 6

3β-(3-(1-Piperazinyl)propoxy)-17β-(3-furyl)-5β-androstan-14β-ol (I-af)

To a mixture of 0.10 g of 17β-(3-furyl)-5β-androstane-3β,14β-diol (II-a: Ref. comp.) (Minato H. and Nagasaki T., *J. Chem. Soc.* (C), 1966, 377)and 0.078 g of sodium hydride under nitrogen, 0.50 g of 4-acetil-1-(3-chloropropyl)-piperazine were added and the resulting suspension was heated at 90° C. for 3 hrs. To the cooled mixture, 10 ml of water were added, the mixture was extracted with methylene chloride, the organic layer was washed with water, dried over anhydrous sodium sulfate and evaporated to dryness under reduced pressure. A solution of the crude product in 5 ml of methanol and 5 ml of sodium hydroxide 30% was heated at 60° C. for 24 hrs. The organic solvent was distilled under reduced pressure and the aqueous mixture was extracted with methylene chloride. The organic phase was washed with water, dried over anhydrous sodium sulfate and evaporated to dryness under reduced pressure. The crude product was purified by flash-chromatography (SiO₂) using methylene chloride/methanol 90/10 as eluant to give 0.060 g of the title compound (I-af), as a white semisolid paste.

¹H-NMR (300 MHz, CDCl₃, ppm from TMS): 0.70 (3H, s); 0.90 (3H, s); 2.38–2.48 (2H, t); 2.48–2.58 (4H, m); 2.72 (1H, dd); 2.94–3.05 (4H, m); 3.37 (2H, t); 3.5.5 (1H, bs); 6.45 (1H, bs); 7.18 (1H, bs); 7.28 (1H, bs).

EXAMPLE 7

3β-(2-(2-(1-Pyrrolidinyl)ethylamino)ethoxy-17β-(3-furyl)-5β-androstan-14β-ol (I-ag)

To a solution of 0.90 g of 3β-(2-hydroxyethoxy)-17β-(3-furyl)-5β-andostran-14β-ol, prepared as an intermediate in Ex.1, in 9 ml of dry pyridine, 0.64 g of tosyl chloride were slowly added at room temperature. After 5 hrs stirring, 10 ml of water and 50 ml of ethyl acetate were added, the organic layer was washed with water and dried over anhydrous sodium sulfate to give 1.2 g of 3β-(2-tosyloxyethoxy)-17β]-(3-furyl)-5β-androstan-14β5-ol as a white solid.

¹H-NMR (300 MHz, CDCl₃, ppm from TMS): 0.71 (3H, s); 0.90 (3H, s); 2.48 (3H, s); 2.74 (1H, dd); 3.52–3.62 (3H, m); 4.15–4.20 (2H, m); 6.46 (1H, bs); 7.20 (1H, bs); 7.30–7.38 (3H, m); 7.78–7.83 (d, 2H).

To a solution of 0.20 g of 315-(2-tosyloxyethoxy)-17β-(3-furyl)-5β-androstan-14β-ol in 2 ml of absolute ethanol 0.15 g of 1-(2-aminoethyl)pyrrolidine were added. The solution was kept at reflux under nitrogen for 3 hrs, then 10 ml of water were added. The residue was extracted with methylene chloride, the organic layer was washed with water to neutral pH, dried over anhydrous sodium sulfate and evaporated to dryness under reduced pressure. The crude residue was purified by flash-chromatography (SiO₂) using methylene chloride/methanol 95/5 as eluant to give 0.15 g of the title compound (I-ag).

¹H-NMR (300 MHz, CDCl₃, ppm from TMS): 0.70 (3H, s); 0.90 (3H, s); 2.5–2.9 (11H, m); 3.45–3.65 (3H, m); 6.48 (1H, bs); 7.20 (1H, bs); 7.32 (1H, bs).

EXAMPLE 8

3β-(2-(2-(1-Pyrrolidinyl)ethoxy)ethoxy), 17β-(3-furyl)-5β-androstan-14β-ol (I-ah)

To a suspension of 0.13 g of NaH (60% dispersion in mineral oil) in 15 ml of anhydrous dimethylformamide, 0.37 g of 1-(2-hydroxyethyl)pyrrolidine were added at room temperature in a nitrogen atmosphere. The mixture was kept at reflux for 2 hrs, then 0.90 g of 3β-(2-tosyloxy-ethoxy)-17β-(3-furyl)-5β-androstan-14β-ol, prepared as an intermediate in Ex. 7, were added. The mixture was kept at reflux temperature for 4 hrs; then 50 ml of water were added cautiously. The residue was extracted with methylene chloride, the organic layer was washed with water, dried over anhydrous sodium sulfate and evaporated to dryness under reduced pressure. The crude product was purified by flash-chromatography (SiO₂) using acetone/methanol 85/15 as eluant to give 0.70 g of the title compound (I-ah) as a light yellow solid.

¹H-NMR (300 MHz, CDCl₃, ppm from TMS): 0.71 (3H, s); 0.91 (3H, s); 2.52–2.67 (4H, m); 2.67–2.78 (3H, m); 3.51–3.58 (2H, m); 3.58–3.68 (5H, m); 6.40 (1H, bs); 7.20 (1H, bs); 7.30 (1H, bs)

EXAMPLE 9

3β-(2-(2-(1-Pyrrolidinyl)ethylthio)ethoxy)-17β-(3-furyl)-5β-androstan-14β-ol (I-al)

To a solution of 0.28 g of 1-(2-mercaptoethyl)pyrrolidine in 20 ml of dimethylformamide, 0.086 g of sodium hydride (60% dispersion in mineral oil) were added under nitrogen atmosphere, and the mixture stirred at room temperature for half an hr; a DMF solution of 1.0 g of 3β-(2-tosyloxyethoxy)-17β-(3-furyl)-5β-androstan-14β-ol, prepared as described in Ex. 7, was added and the mixture was stirred for another 4 hrs; the reaction mixture was quenched with water and extracted with methylene chloride. The organic layer was washed with water, dried over anhydrous sodium sulfate and evaporated to dryness under reduced pressure. The crude product was purified by flash-cromatography (SiO$_2$) using methylene chloride/methanol 95/5 as eluant and 0.90 g of the title compound (I-ai) as a white amorphous solid.

$^1$H NMR (300 MHz, CDCl$_3$, ppm from TMS): 0.70 (3H, s); 0.92 (3H, s); 2.20–2.80 (11H, m); 3.58 (2H, m); 3.67 (1H, bs); 6.41 (1H, bs); 7.20 (1H, bs); 7.30 (1H, bs).

EXAMPLE 10

3β-(2-(3-Dimethylaminopropoxy)-ethoxy)-17β-(3-furyl)-5β-androstan-14β-ol (I-aj)

The title compound (I-aj) (0.13 g) was obtained as a colourless oil from 3β-(2-tosyloxyethoxy)-17β-(3-furyl)-5β-androstan-14β-ol (0.20 g), prepared as described in Ex. 7, using the same procedure described in Ex. 8.

$^1$H-NMR (300 MHz, CDCl$_3$, ppm from TMS): 0.72 (3H, s); 0.93 (3H, s); 2.22 (6H, s); 2.31–2.38 (2H, t); 2.74 (1H, dd); 3.48–3.62(6H, m); 3.67 (1H, bs); 6.44 (1H, bs); 7.20 (1H, bs); 7.30 (1H, bs).

EXAMPLE 11

3β-(2-(N-methyl-1-pyrrolydinium)ethoxy)-17β-(3-furyl)-5β-androstan-14β-ol iodide (I-ak)

To a 0.037 g of potassium carbonate in 15 ml of methanol, 0.12 g of 3β-(2-(1-pyrrolydinyl)ethoxy)-17β-(3-furyl)-5β-androstan-14β-ol (I-ad) and 0.019 ml of methyl iodide were added at room temperature. After 6 hrs the methanol was evaporated at reduced pressure. The residue was dissolved in methylene chloride, the organic layer was washed with water, dried over anhydrous sodium sulfate and evaporated to dryness under reduced pressure to give 0.12 g of the title compound (I-ak), as a white solid which was not submitted to a further purification.

$^1$H-NMR (300 MHz, CDCl$_3$, ppm from TMS): 0.70 (3H, s); 0.92 (3H, s); 2.74 (1H, dd); 3.47 (3H, s); 3.75 (1H, bs); 3.78–4.10 (8H, m); 6.45 (1 H, bs); 7.20 (1 H, bs); 7.32 (1 H, bs).

EXAMPLE 12

3β-(2-Guanidinoethoxy)-17β-(3-furyl)-5β-androstan-14 β-ol nitrate (I-al)

To a solution of 0.17 g of 3β-(2-aminoethoxy)-17β-(3-furyl)-5β-androstan-14β-ol (I-aa) in 12 ml of absolute ethanol 0.090 g of 3,5-dimethyl-1-pyrazolylformamidinium nitrate were added and the mixture was kept at reflux for 7 hrs; the ethanol was concentrated under reduced pressure and 0.18 g of the title compound (1-al) crystallized as a white solid.

$^1$H NMR: (300 MHz, DMSO-d6, ppm from TMS): 0.58 (3H, s); 0.85 (3H, s); 2.57–2.67 (1H, m); 3.2–3.35 (2H, m); 3.43–3.47 (2H, m); 3.62 (1H, bs); 6.42 (1H, bs); 7.32(1H, bs); 7.43 (1H, bs).

EXAMPLE 13

3β-(3-Guanidinopropoxy)-17β-(3-furyl)-5β-androstan-14β-ol nitrate (I-am)

To a solution of 0.10 g of 3β-(3-aminopropoxy)-17β-(3-furyl)-5β-androstan-14β-ol (I-ab) in 7 ml of absolute ethanol 0.060 g of 3,5-dimethyl-1-pyrazolylformamidinium nitrate were added and the mixture was kept at reflux temperature for 24 hrs; the ethanol was concentrated under reduced pressure and 0.090 g of the title compound (I-am) crystallized as a white solid.

$^1$H NMR: (300 MHz, DMSO-d6, ppm from TMS): 0.58 (3H, s); 0.85 (3H, s); 2.50–2.60(1H, m); 3.14 (2H, m); 3.35 (2H, m); 3.54 (1H, bs); 3.82 (1H, bs); 6.50 (1H, bs); 7.30 (1H, bs); 7.46 (1H, bs).

EXAMPLE 14

3β-(2-Methylaminoethoxy)-17β-(3-furyl)-5β-androstan-14β-ol (I-an)

To 7 ml of a solution of methylamine 3.2 M in methanol, 0.090 g of 3β-(2-tosyloxyethoxy)-17β-(3-furyl)-5β-androstan-14β-ol, prepared as an intermediate in Ex.7, were added. The solution was kept at reflux under nitrogen for 11 hrs, then was evaporated. The resulting solid was washed with n-hexane to give 0.045 g of the title compound (I-an) as a light yellow pasty solid.

$^1$H-NMR (300 MHz, CDCl$_3$, ppm from TMS): 0.72 (3H, s); 0.92 (3H, s); 2.54 (3H, s); 2.74 (1H, dd); 2.82 (2H, t); 3.00–3.08 (2H, m); 3.68 (1H, bs); 6.47 (1H, s); 7.22 (1H, s); 7.33 (1H, s).

EXAMPLE 15

3β-(2,3-Diaminopropoxy)-17β-(3-furyl)-5β-androstan-14β-ol (I-ao)

To a mixture of 0.70 g of N-Methylmorpholine-N-oxide, 6.5 ml of water, 13.7 ml of acetone and 1.64 ml of a 0.06 M ethereal osmium tetroxide solution, 2.0 g of 3β-prop-2-enoxy-17β(3-furyl)-5β-androstan-14β-ol, prepared as an intermediate in Ex.2, dissolved in 29 ml of tert-butanol were added at room temperature. The mixture was left on standing for 20 hrs, 50 ml of a saturated sodium hydrosulfite solution and 2.0 g of celite were added, the mixture was stirred for 2 hrs and then filtered. The organic solvent was distilled under reduced pressure, the aqueous phase was extracted with methylene chloride, the organic layer was dried over anhydrous sodium sulfate and evaporated to dryness under reduced pressure. The crude product was purified by flash-chromatography (SiO$_2$) using n-hexane/ethyl acetate 20/80 as eluant to give 1.8 g of 3β-(2,3-dihydroxypropoxy)-17β-(3-furyl)-5β-androstan-14β-ol as a white solid.

$^1$H NMR (300 MHz, CDCl$_3$, ppm from TMS): 0.70 (3H, s); 0.95 (3H, s); 2.32–2.48 (1H, m); 2.67–2.82 (2H, m); 3.46–3.60 (2H, m); 3.68 (1H, bs); 3.70–3.79 (2H, m); 3.82–3.92 (1H, m); 6.48 (1H, bs); 7.20 (1H, bs); 7.32 (1H, bs).

To a solution of 0.92 g of 3β-(2,3-dihydroxypropoxy)-17β(3-furyl)-5β-androstan-14βol, in 6.6 ml of dry pyridine, 0.84 g of tosyl chloride were added at a temperature of 0° C. After 5 hrs 15 ml of water and 60 ml of ethyl, acetate were added, the organic layer was washed with water, dried over anhydrous sodium sulfate and evaporated to dryness under reduced pressure. The crude product was purified by flash-chromatography (SiO$_2$) using n-hexane/ethyl acetate 80/20 as eluant to give 1.3 g of 3β-(2,3-ditosyloxypropoxy)-17β-(3-furyl)-5β-androstan-14β-ol as a white solid.

¹H NMR (300 MH$_z$, CDCl$_3$, ppm from TMS): 0.71 (3H, s); 0.88 (3H, s); 2.45 (6H, bs); 2.74 (1H, dd); 3.45–3.55 (3H, m); 4.05–4.18 (2H, m); 4.62 (1H, bs); 6.47 (1H, bs); 7.22 (1H, bs); 7.30–7.40 (5H, m); 7.70–7.82 (4H, m).

To a solution of 1.3 g of 3β-(2,3-ditosyloxypropoxy)-17β-(3-furyl)-5β-androstan-14β-ol in 10 ml of dimethylsulfoxide 1.1 g of sodium azide were added at room temperature. The solution was kept at reflux for 3 hrs, then 5 ml of water were added and the residue was extracted with methylene chloride. The organic layer was washed with water, dried over anhydrous sodium sulfate and evaporated to dryness under reduced :pressure. The crude product was purified by flash-chromatography (SiO$_2$)using n-hexane/ethyl acetate 80/20 as eluant to give 0.75 g 3β-(2,3-diazidopropoxy)-17β-(3-furyl)-5β-androstan-14β-ol.

¹H NMR: (300 MHz, CDCl$_3$, ppm from TMS): 0.72 (3H, s); 0.94 (3H, s); 2.74 (1H, m); 3.4–3.7 (5H, m); 3.68 (1H, bs); 6.48 (1H, bs); 7.20 (1 H, bs); 7.31 (1 H, bs).

A solution of 0.44 g of 3β-(2,3-diazidopropoxy)-17β-(3-furyl)-5 β-androstan-14β-ol in 9 ml of diethyl ether is added to a suspension of 0.20 g of lithium aluminium hydride in 6 ml of diethyl ether.

The mixture was kept at reflux for 12 hrs then in succession were added 0.44 ml of water, 0.44 ml of sodium hydroxyde (water solution 10%) and 1.76 ml of water. The mixture was filtered over a celite cake, the organic solution was washed with water, dried over sodium sulfate and evaporated to dryness under reduced pressure. The crude residue was purified by flash-chromatography (SiO$_2$) using methylene chloride/methanol/30% ammonia solution 90/10/1 as eluant to give 0.29 g of the title compound (I-ao) a white solid.

¹H NMR (300 MH$_z$, CDCl$_3$, ppm from TMS): 0.70 (3H, s); 0.90 (3H, s); 2.70–3.50 (6H, m); 3.68 (1H, bs); 6.48 (1H, bs); 7.20 (1H, bs); 7.32 (1H, bs).

EXAMPLE 16

3β(2,3-Bis(1-pyrrolidinyl)propoxy)-17β-(3-furyl)-5β-androstan-14β-ol (I-ap)

To a solution of 0.16 g of 3β-(2,3-ditosyloxypropoxy)-17β-(3-furyl)-5β-androstan-14β-ol, prepared as an intermediate in Ex.15, in 1.5 ml of absolute ethanol, 1 g of pyrrolidine were added at room temperature. The solution was kept at reflux for 3 hrs, then 10 ml of water were added and the residue was extracted with methylene chloride. The organic layer was washed with water to neutral pH, dried over anhydrous sodium sulfate and evaporated to dryness under reduced pressure. The crude product was purified by flash-chromatography (SiO$_2$) using methylene chloride/methanol 95/5 as eluant to give 0.92 g of the title compound (1-ap) as a light yellow amorphous solid.

¹H NMR (300 MHz, CDCl$_3$, ppm from TMS): 0.72 (3H, s); 0.92 (3H, s); 2.51–2.79 (12H, m); 3.49–3.65 (3H, m); 6.47 (1H, bs); 7.22 (1H, bs); 7.32 (1H, bs).

EXAMPLE 17

3β,14β-Bis(2-(1-pyrrolidinyl)ethoxy)-17β-(3-furyl)-5β-androstane (I-aq)

The title compound (I-aq) (0.12 g) was obtained as a white solid from 17β-(3-furyl)-5β-androstane-3β,14β-diol (II-a: Ref. comp.) (Minato H. and Nagasaki T., *J. Chem. Soc.* (C), 1966, 377) (0.10 g) using the same procedure described in Ex. 4, but the reaction was kept at reflux temperature for 24 hrs, instead of 4 hrs.

¹H-NMR (300 MHz, CDCl$_3$, ppm from TMS): 0.78 (3H, s); 0.94 (3H, s); 2.50–2.80 (12H, m); 3.48–3.56 (2H, m); 3.58–3.70 (3H, m); 6.42 (1H, bs); 7.2 (1H, bs); 7.3 (1H, bs).

EXAMPLE 18

3β-(3-Aminoproproxy)-14β-methoxy-17β-(3-furyl)-5β-androstane (I-ar)

The title compound (I-ar) (0.22 g) was obtained as a white solid from 14β5-methoxy-17β-(3-furyl)-5β-androstan-3β-ol (II-c, Prep. 2) (1.0 g) using the same procedure described in Ex. 2.

¹H-NMR (300 MHz, CDOD$_3$, ppm from TMS): 0.78 (3H, s); 1.00 (3H, s); 2.70–2.85 (3H, m); 3.35 (3H, m); 3.46 (3H, m); 3.62 (1H, bs); 6.40 (1H, bs); 7.18 (1H, bs); 7.35 (1H, bs).

EXAMPLE 19

3β-(2-(1-Pyrrolydinyl)ethoxy)-14β-methoxy-17β-(3-furyl)-5β-androstane oxalate (I-as)

To a suspension of 0.50 g of NaH (60% dispersion in mineral oil) in 85 ml of dry tetrahydrofuran 0.45 g of 14β-methoxy-17β-(3-furyl)-5β-androstan-3β-ol (II-c, Prep. 2) were added at room temperature in a nitrogen atmosphere. The mixture was kept at reflux for 6 hrs, then 2.0 g of 1-(2-chloroethyl)pyrrolidine were added; the suspension was kept at reflux temperature for 4 hrs, 50 ml of water were added cautiously and the tetrahydrofuran was distilled under reduced pressure. The residue was extracted with methylene chloride, the organic layer was dried over anhydrous sodium sulfate and evaporated to dryness under reduced pressure. The crude product was purified by flash-chromatography (SiO$_2$) using methylene chloride/methanol 70/30 as eluant to give the pure compound that was successively treated with oxalic acid to give 0.30 g of the title compound (I-as) as a white solid.

¹H-NMR (300 MHz, CDOD$_3$, ppm from TMS): 0.78 (3H, s); 1.0 (3H, s); 2.72 (1H, m); 3.35 (3H, s); 3.40 (6H, m); 3.75 (3H, m); 6.40 (1H, bs); 7.18 (1H, bs); 7.35 (1H, bs).

EXAMPLE 20

3β-(3-Aminopropoxy)-17β-(3-furyl)-androst-4-en-14β-ol (I-at)

The title compound (I-at) (0.15 g) was obtained as a white solid from 17β-(3-furyl)-androst-4-ene-3β,14β-diol (prepared from canarigenin as described in Minato H., and Nagasaki T., *J. Chem. Soc.* (C), 1966, 377)(1.0 g) using the same procedure described in Ex. 2.

¹H-NMR (300 MHz, CDCl$_3$, ppm from TMS): 0.71 (3H, s); 1.09 (3H, s); 2.70–2.85 (3H, m); 3.46 (2H, m); 4.01 (1H, m); 5.40 (1H, bs); 6.53 (1H, bs); 7.20 (1H, bs); 7.35 (1H, bs).

EXAMPLE 21

3β-(2-(1-Pyrrolidinyl)ethoxy)-17β-(3-furyl)-androst-4-en-14β-ol oxalate (I-au)

The title compound (I-au) (0.25 g) was obtained as a white solid from 17β-(3-furyl)-androst-4-ene-3β,14β-diol (prepared from canarigenin as described in Minato H., and Nagasaki T., *J. Chem. Soc.* (C), 1966, 377) (0.28 g) using the same procedure described in Ex. 19.

¹H-NMR (300 MHz, CDCl$_3$, ppm from TMS): 0.71 (3H, s); 1.09 (3H, s); 2.72 (1H, dd); 3.22–3.65 (6H, m);

3.78 (2H, m); 4.01 (1H, m); 5.40 (1H, bs); 6.53 (1H, bs); 7.20 (1H, bs); 7.35 (1H, bs).

EXAMPLE 22

3β-(Aminopropoxy)-17β-(3-furyl)-androst-5-en-14β-ol (I-av)

The title compound (I-av) (0.090 g) was obtained as a white solid from 17β-(3-furyl)-androst-5-ene-3β,14β-diol (prepared from xysmalogenin as described in Minato H., and Nagasaki T., *J. Chem. Soc.* (C), 1966, 377)(0.70 g) using the same procedure described in Ex. 2.

$^1$H-NMR (300 MHz, CDCl$_3$, ppm from TMS): 0.51 (3H, s); 0.98 (3H, s); 2.70–2.85 (3H, m); 3.10–3.25 (1H, m); 3.46 (2H, m); 5.38 (1H, bs); 6.30 (1H, bs); 7.28 (1H, bs); 7.38 (1H, bs).

EXAMPLE 23

3β-(2-(1-Pyrrolidinyl)ethoxy)-17β-(3-furyl)-androst-25-en-14β-ol (I-aw)

The title compound (I-aw) (0.26 g) was obtained as a white solid from 17β-(3-furyl)-androst-5-ene-3β,14β-diol (prepared from xysmalogenin as described in Minato H., and Nagasaki T., *J. Chem. Soc.* (C), 1966, 377) (0.30 g) using the same procedure described in Ex. 4.

$^1$H-NMR (300 MHz, CDCl$_3$, ppm from TMS): 0.51 (3H, s); 0.98 (3H, s); 2.50–2.60 (4H, m); 2.69 (2H, t); 3.10–3.25 (1H, m); 3.63 (1H, t); 5.38 (1H, bs); 6.30 (1H, bs); 7.28 (1H, bs); 7.38 (1H, bs).

EXAMPLE 24

3β-(3-Aminopropoxy)-17β-(3-furyl)-5α-androstan-14β-ol (I-ax)

The title compound (1-ax) (0.030 g) was obtained as a light jellow solid from 17β-(3-furyl)-5α-androstane-3β,14β-diol (prepared from uzarigenin as described in Minato H., and Nagasaki T., *J. Chem. Soc.* (C), 1966, 377)(0.30 g) using the same procedure described in Ex. 2.

$^1$H-NMR (300 MHz, CDCl$_3$, ppm from TMS): 0.51 (3H, s); 0.98 (3H, s); 2.70–2.85 (3H, m); 3.28 (1H, m); 3.46 (2H, m); 6.48 (1H, bs); 7.21 (1H, bs); 7.32 (1H, bs).

EXAMPLE 25

3β-(2-(1-Pyrrolidinyl)ethoxy)-17β-(3-furyl)-5α-androstan-14β-ol (I-ay)

The title compound (I-ay) (0.070 g) was obtained as a white solid from 17β-(3-furyl)-5a-androstane-3β,14β-diol (prepared from uzarigenin as described in Minato H., and Nagasaki T., *J. Chem. Soc.* (C), 1966, 377) (0.10 g) using the same procedure described in Ex. 4.

$^1$H-NMR (300 MHz, CDCl$_3$, ppm from TMS): 0.51 (3H, s); 0.98 (3H, s); 2.58 (4H, bs); 2.65–2.75 (3H, m) 3.28 (1H, m); 3.52 (2H, m); 6.48 (1H, bs); 7.21 (1H, bs); 7.32 (1H, bs).

EXAMPLE 26

3β-(3,Aminopropoxy)-14β,15β-epoxy-17β-(3-furyl)-5β-androstane (I-az)

The title compound (I-az) (0.090 g) was obtained as a white solid from 14β,15β-epoxy-17β-(3-furyl)-5β-androstan-3β-ol (E. Yoshii et al., *Chem. Pharm. Bull,* 1976,24,3216)(0.60 g) using the same procedure described in Ex. 2.

$^1$H-NMR (300 MHz, CDCl$_3$, ppm from TMS): 0.76 (3H, s); 1.00 (3H, s); 2.36 (1H, m); 2.70–2.85 (3H, m); 3.46 (2H, m); 3.56 (1H, bs); 3.65 (1H, bs); 6.42 (1H, bs); 7.18 (1H, bs); 7.29 (1H, bs).

EXAMPLE 27

3β-(2-(1-Pyrrolidinyl)ethoxy)-14β,15β-epoxy-17β-(3-furyl)-5β-androstane oxalate (I-ba)

The title compound (1-ba) (0.60 g) was obtained as a white solid from 14β,15β-epoxy-17β-(3-furyl)-5β-androstan-3β-ol (E. Yoshii et al., *Chem. Pharm. Bull.,* 1976, 24, 3216) (0.75 g) using the same procedure described in Ex. 19.

$^1$H-NMR (300 MHz, CDCl3, ppm from TMS): 0.76 (3H, s); 1.00 (3H, s); 2.11 (4H, bs); 2.36 (1H, m); 2.71 (1H, d); 3.42 (2H, m); 3.56 (1H, s); 3.71 (3H, bs); 6.42 (1H, bs); 7.18 (1H, bs); 7.29 (1H, bs).

EXAMPLE 28

3β-(3-Aminopronoxy)-14β,15β-epoxy-17β-(3-furyl)-androst-4-ene (I-bb)

The title compound (I-bb) (0.10 g) was obtained as a white solid from 14β,15β-epoxy-17β-(3-furyl)-androst-4-en-3β-ol (prepared from 3β-hydroxy-14β,15β-epoxy-carda-4,20(22)-dienolide, W. Fritsch et al., *Ann. Chem.,* 1969, 727, 110, E. Yoshii et al., *Chem. Pharm. Bull,* 1976, 24, 3216)(0.60 g) using the same procedure described in Ex. 2.

$^1$H-NMR (300 MHz, CDCl$_3$, ppm from TMS): 0.71 (3H, s); 1.00 (3H, s); 2.36 (1H, m); 2.65–2.75 (3H, m); 3.46 (2H, m); 3.56 (1H, bs). 4.01 (1H, m); 5.40 (1H, bs); 6.53 (1H, bs); 7.20 (1H, bs); 7.35 (1H, bs).

EXAMPLE 29

3β-(2-(1-Pyrrolidinyl)ethoxy)-14β,15β-epoxy-17β-(3-furyl)-androst-4-ene (I-bc)

The title compound (I-bc) (0.28 g) was obtained as a white solid from 14β,15β-epoxy-17β-(3-furyl)-androst-4-en-3β-ol (prepared from 3β-hydroxy-14β,15β-epoxy-carda-4,20(22)-dienolide, W. Fritsch et al., *Ann. Chem.,* 1969, 727, 110, E. Yoshii et al., Chem. Pharm. Bull, 1976, 24, 3216) (0.30 g) using the same procedure described in Ex. 4.

$^1$H-NMR (300 MHz, CDCl$_3$, ppm from TMS): 0.71 (3H, s); 1.00 (3H, s); 2.36 (1H, m); 2.58 (4H, bs); 2.65–2.75 (3H, m); 3.50–3.60 (3H, m). 4.01 (1H, m); 5.40 (1H, bs); 6.43 (1H, bs); 7.18 (1H, bs); 7.29 (1H, bs).

EXAMPLE 30

3β-(3-Aminopropoxy)-14β,15β-epoxy-17β-(3-furyl)-androst-5-ene (I-bd)

The title compound (I-bd) (0.090 g) was obtained as a colourless oil from 14β,15β-epoxy-17β-(3-furyl)-androst-5-en-3β-ol (prepared from xysmalogenin as described in Fritsch W. et al., *Ann. Chem.,* 1969, 727, 110, E. Yoshii et al., *Chem. Pharm. Bull,* 1976, 24, 3216) (0.60 g) using the same procedure described in Ex. 2.

$^1$H-NMR (300 MHz, CDCl$_3$, ppm from TMS): 0.51 (3H, s); 1.07 (3H, s); 2.70–2.85 (3H, m); 3.15–3.25 (1H, m); 3.46 (2H, m); 3.56 (1H, bs); 5.40 (1H, bs); 6.48 (1H, bs); 7.20 (1H, bs); 7.35 (1H, bs).

EXAMPLE 31

3β-(2-(1-Pyrrolidinyl)ethoxy)-14β,15β-epoxy-17β-(3-furyl)-androst-5-ene (I-be)

The title compound (I-be) (0.30 g) was obtained as a white solid from 14β,15β-epoxy-17β-(3-furyl)-androst-5-en-3β-ol (prepared from xysmalogenin as described in W. Fritsch et al., *Ann. Chem.,* 1969, 727, 110, E. Yoshii et al., *Chem. Pharm. Bull*, 1976, 24, 3216) (0.30 g) using the same procedure described in Ex. 4.

$^1$H-NMR (300 MHz, CDCl$_3$, ppm from TMS): 0.51 (3H, s); 1.07 (3H, s); 2.51–2.63 (4H, bs); 2.65–2.80 (3H, m); 3.15–3.25 (1H, m); 3.51–3.61 (3H, m). 5.40 (1H, bs); 6.48(1H, bs); 7.20 (1H, bs); 7.35 (1H, bs).

EXAMPLE 32

3β-(3-Aminopropoxy)-14β,15β-epoxy-17β-(3-furyl)-5 α-androstane (I-bf)

The title compound (I-bf) (0.020 g) was obtained as a white solid from 14β,15β-epoxy-17β-(3-furyl)-5α-androstan-3β-ol (prepared from 3β-hydroxy-14β,15β-epoxy-5α-card-20(22)-enolide, DE Pat. 1807585, E. Yoshii et al., Chem. Pharm. Bull, 1976, 24, 3216)(0.40 g) using the same procedure described in Ex. 2.

$^1$H-NMR (300 MHz, CDCl$_3$, ppm from TMS): 0.51 (3H, s); 1.00 (3H, s); 2.36 (1H, m); 2.70–2.85 (3H, m); 3.28 (1H, m); 3.46 (2H, m); 3.56 (1H, bs); 6.42(1H, bs); 7.18 (1H, bs); 7.29 (1H, bs).

EXAMPLE 33

3β-(2-(1-Pyrrolidinyl)ethoxy)-14β,15β-epoxy-17β-(3-furyl)-5α-androstane (I-bg)

The title compound (I-bg) (0.080 g) was obtained as a light yellow solid from 14β,15β-epoxy-17β-(3-furyl)-5α-androstan-3β-ol (prepared from 3β-hydroxy-14β,15β-epoxy-5α-carda-20(22)-dienolide, DE Pat. 1807585,-E. Yoshii et al., *Chem. Pharm. Bull*, 1976, 24, 3216) (0.10 g) using the same procedure described in Ex. 4.

$^1$H-NMR (300 MHz, CDCl$_3$, ppm from TMS): 0.51 (3H, s); 1.00 (3H, s); 2.36 (1H, m); 2.58 (4H, bs); 2.65–2.75 (3H, m); 3.28 (1H, m); 3.50–3.60 (3H, m); 6.42 (1H, bs); 7.18 (1H, bs); 7.29 (1H, bs).

EXAMPLE 34

3β-(3-Aminopropoxy)-14α,15β-epoxy-17α-(3-furyl)-5β-androstane (I-bh)

The title compound (I-bh) (0.050 g) was obtained as a white solid from 14α,15α-epoxy-17β-(3-furyl)-5β-androstan-3β-ol (prepared from 3β-hydroxy-14α,15α-epoxy-card-20(22)-enolide, Ishii H, *Chem. Pharm. Bull*, 1963, 11, 576, Minato H., and Nagasaki T., *J. Chem. Soc.* (C),1966, 377)(0.35 g) using the same procedure described in Ex. 2.

H$^1$-NMR (300 MHz, CDCl$_3$, ppm from TMS): 0.66 (3H, s); 0.98 (3H, s); 2.65 (1H, dd); 2.72 (2H, m); 3.42–3.55 (3H, m); 3.63 (1H, bs); 6.19 (1H, bs); 7.18 (1H, bs); 7.29 (1H, bs).

EXAMPLE 35

3β-(2-(1-pyrrolidinyl)ethoxy)-14β,15β-epoxy-17β-(3-furyl)-5β-androstane (I-bi)

The title compound (I-bi) (0.085 g) was obtained as a white solid from 14β,15β-epoxy-17β(3-furyl)-5β-androstan-3β-ol (prepared from 3β-hydroxy-14α,15α-epoxy-card-20(22)-enolide, Ishii H, *Chem. Pharm. Bull.,* 1963, 11, 576, Minato H., and Nagasaki T., *J. Chem. Soc.* (C), 1966, 377) (0.10 g) using the same procedure described in Ex. 4.

H$^1$-NMR (300 MHz, CDCl$_3$, ppm from TMS): 0.66 (3H, s); 0.98 (3H, s); 2.55–2.77 (7H, m); 3.50–3.60 (3H, m); 3.63 (1H, bs); 6.19 (1H, bs); 7.18 (1H, bs); 7.29 (1H, bs).

EXAMPLE 36

3β-(2-(1-Pyrrolidinyl)ethoxy)-17β-(3-furyl)-5β,14β-androstane (I-bi)

The title compound (I-bj) (0.050 g) was obtained as a white solid from 17β-(3-furyl)-5β,14β-androstan-3β-ol (prepared from 3β-hydroxy-5β,14β-card-20(22)-enolide, Naidoo K., *J. Pharm. Science.*, 1974, 23, 1391, Minato H., and Nagasaki T., *J. Chem. Soc.* (C), 1966, 377) (0.070 g) using the same procedure described in Ex. 4.

H$^1$-NMR (300 MHz, CDCl$_3$, ppm from TMS): 0.71 (3H, s); 0.92 (3H, s); 2.52–2.78 (7H, m); 3.52 (2H, m); 3.63 (1H, bs); 6.21 (1H, bs); 7.14 (1H, bs); 7.32 (1H, bs).

EXAMPLE 37

3β-(3-Aminopropoxy)-17β-(3-furyl)-androst-4-ene (I-bk)

The title compound (I-bk) (0.15 g) was obtained as a white solid from 17β-(3-furyl)-androst-4-en-3β-ol (prepared from 17β-(3-furyl)-androst-4-en-3-one, described in U.S. Pat. No. 3436390, with known procedures) (0.60 g) using the same procedure described in Ex. 2.

H$^1$-NMR (300 MHz, CDCl$_3$, ppm from TMS): 0.71 (3H, s); 0.82 (3H, s); 2.45 (1H, m); 2.83 (2H, m); 3.46 (2H, m); 4.01 (1H, m); 6.28 (1H, bs); 7.18 (1H, bs); 7.36 (1H, bs).

EXAMPLE 38

3β-(2-(1-Pyrrolidinyl)ethoxy)-17β-(3-furyl)-androst-4-ene (I-bl)

The title compound (I-bl) (0.27 g) was obtained as a white solid from 17β-(3-furyl)-androst-4-en-3β-ol (prepared from 17β-(3-furyl)-androst-4-en-3-one, described in U.S. Pat. No. 3436390, with known procedures) (0.30 g) using the same procedure described in Ex. 4.

H$^1$-NMR (300 MHz, CDCl3, ppm from TMS): 0.71 (3H, s); 0.82 (3H, s); 2.45 (1H, m); 2.58 (4H, bs); 2.65–2.75 (2H, m); 3.52 (2H, m); 4.01 (1H, m); 6.28 (1H, bs); 7.18 (1H, bs); 7.36 (1H, bs).

EXAMPLE 39

3β-(3-Aminopropoxy)-17β-(3-furyl)-androst-5-ene (I-bm)

The title compound (I-bm) (0.13 g) was obtained as a white solid from 17β-(3-furyl)-androst-5-en-3β-ol (prepared from 3β-hydroxy-androst-5-en-17-one in the same manner described in U.S. Pat. No. 3436390) (0.60 g) using the same procedure described in Ex. 2.

$^1$H-NMR (300 MHz, CDCl$_3$, ppm from TMS): 0.51 (3H, s); 0.98 (3H, s); 2.83 (2H, m); 3.10–3.25 (1H, m); 3.53 (2H, m); 5.38 (1H, bs); 6.30 (1H, bs); 7.28 (1H, bs); 7.38 (1H, bs).

EXAMPLE 40

3β-(2-(1-Pyrrolidinyl)ethoxy)-17β-(3-furyl)-androst-5-ene (I-bn)

The title compound (I-bn) (0.31 g) was obtained as a white solid from 17β-(3-furyl)-androst-5-en-3β-ol (prepared from 3β-hydroxy-androst-5-en-17-one in the same manner described in U.S. Pat. No. 3436390) (0.30 g) using the same procedure described in Ex. 4.

$^1$H-NMR (300 MHz, CDCl$_3$, ppm from TMS): 0.51 (3H, s); 0.98 (3H, s); 2.50–2.60 (4H, m); 2.69 (2H, t); 3.10–3.25 (1H, m); 3.63 (1H, t); 5.38 (1H, bs); 6.30 (1H, bs); 7.28 (1H, bs); 7.38 (1H, bs).

EXAMPLE 41

3β-(3-Aminopropoxy)-17β-furyl)-5α-androstane (I-bo)

The title compound (I-bo) (0.17 g) was obtained as a white solid from 17β-(3-furyl)-5α-androstan-3β-ol (U.S. Pat. No. 3436390) (0.60 g) using the same procedure described in Ex. 2.

$^1$H-NMR (300 MHz, CDCl$_3$, ppm from TMS): 0.51 (3H, s); 0.82 (3H, s); 2.45 (1H, m); 2.83 (2H, m); 3.28 (1H, m); 3.46 (2H, m); 6.28 (1H, bs); 7.18 (1H, bs); 7.36 (1H, bs).

EXAMPLE 42

3β-(2-(1-Pyrrolidinyl)ethoxy)-17β-(3-furyl)-5α-androstane (I-bp)

The title compound (I-bp) (0.15 g) was obtained as a white solid from 17β-(3-furyl)-5α-androstan-3β-ol (U.S. Pat. No. 3436390) (0.15 g) using the same procedure described in Ex. 4.

$^1$H-NMR (300 MHz, CDCl$_3$, ppm from TMS): 0.51 (3H, s); 0.82 (3H, s); 2.45 (1H, m); 2.58 (4H, bs); 2.70 (2H, m); 3.28 (1H, m); 3.52 (2H, m); 6.28 (1H, bs); 7.18 (1H, bs); 7.36 (1H, bs).

EXAMPLE 43

3α-(3-Aminopropoxy)-17β-(3-furyl)-5β-androstan-14β-ol (I-bq)

The title compound (I-bq) (0.15 g) was obtained as a white solid from 17β-(3-furyl)-5β-androstane-3α,14β-diol (Humber D. et al., Steroids, 1983, 42, 189) (0.60 g) using the same procedure described in Ex. 2.

$^1$H-NMR (300 MHz, CDCl$_3$, ppm from TMS): 0.71 (3H, s); 0.97 (3H, s); 2.74 (1H, dd); 2.82 (2H, m); 3.28 (1H, m); 3.46 (2H, m); 6.48 (1H, bs); 7.21 (1H, bs); 7.32 (1H, bs).

EXAMPLE 44

3α-(2-(1-Pyrrolydinyl)ethoxy)-17β-(3-furyl)-5β-androstan-14β5-ol (I-br)

The title compound (I-br) (0.34 g) was obtained as a white solid from 17β-(3-furyl)-5β-androstane-3α,14β-diol (Humber D. et al., Steroids, 1983, 42, 189) (0.35 g) using the same procedure described in Ex. 4.

$^1$H-NMR (300 MHz, CDCl$_3$, ppm from TMS): 0.70 (3H, s); 0.92 (3H, s); 2.50-2.62 (4H, m); 2.65-2.82 (3H, m); 3.20-3.35 (1H, m); 3.58-3.68 (2H, m); 6.45 (1H, bs); 7.20 (1H, bs); 7.30 (1H, bs).

EXAMPLE 45

3α-(3-Aminopropoxy)-14β,15β-epoxy-17β-(3-furyl)-5β-androstane (I-bs)

The title compound (I-bs) (0.14 g) was obtained as a white solid from 14β,15β-epoxy-17β-(3-furyl)-5β-androstan-3a-ol (II-b, Prep. 1)(0.60 g) using the same procedure described in Ex. 2.

$^1$H-NMR (300 MHz, CDCl$_3$, ppm from TMS): 0.76 (3H, s); 1.00 (3H, s); 2.36 (1H, m); 2.70-2.85 (3H, m); 3.28 (1H, m); 3.46 (2H, m); 3.56 (1H, bs); 6.42 (1H, bs); 7.18 (1H, bs); 7.29 (1H, bs).

EXAMPLE 46

3α(2-(1-Pyrrolidinyl)ethoxy)-14β,15β-epoxy-17β-(3-furyl)-5.15-androstane (I-bt)

The title compound (I-bt) (0.34 g) was obtained as a white solid from 14β,15β-epoxy-17β-(3-furyl)-5β-androstan-3α-ol (II-b, Prep. 1) (0.35 g) using the same procedure described in Ex. 4.

$^1$H-NMR (300 MHz, CDCl$_3$, ppm from TMS): 0.76 (3H, s); 1.00 (3H, s); 2.36 (1H, m); 2.50-2.62 (4H, m); 2.68-2.77 (3H, m); 3.28 (1H, m); 3.50-3.60 (3H, m); 6.4.2 (1H, bs); 7.18 (1H, bs); 7.29 (1H, bs).

EXAMPLE 47

3β-(2-(4-Morpholinoethylthio)-17β-(3-furyl)-5β-androstan-14β-ol oxalate (I-bu)

To a solution of 0.19 g of 3β-mercapto-17β-(3-furyl)-5β-androstan-14β-ol (II-d, Prep. 3) and 0.33 ml of 4-(2-chloroethyl)morpholine in 5.0 ml of tetrahydrofuran under nitrogen atmosphere at room temperature, 0.030 g of sodium hydride (60% dispersion in mineral oil) were added. The reaction mixture was stirred for 40 hrs, diluted with water and extracted with ethyl acetate; the organic layer was dried over sodium sulfate and evaporated to dryness under reduced pressure. The crude product was purified by flash-chromatography (SiO$_2$) using methylene chloride/methanol/30% ammonia solution 95/5/1 as eluant and successively treated with oxalic acid to give 0.20 g of the title compound (I-bu) as a white solid.

$^1$H-NMR (300 MHz, CDCl$_3$, ppm from TMS): 0.72 (3H, s); 0.95 (3H, s); 2.45-2.55 (2H, m); 2.75 (1H, dd); 3.25 (1H, bs); 3.72 (4H, t); 6.48 (1H, bs); 7.21 (1H, bs); 7.32 (1H, bs).

EXAMPLE 48

3β-(2-Aminoethylthio)-17β-(3-furyl)-5β-androstan-14β-ol oxalate (I-bv)

The title compound (I-bv) (0.20 g) was obtained as a white solid from 3β-mercapto-17β-(3-furyl)5β-androstan-14β-ol (II-d, Prep. 3)(0.30 g) using the same procedure described in Ex. 47.

$^1$H-NMR (300 MHz, CDCl$_3$, ppm from TMS): 0.72 (3H, s); 0.95 (3H, s); 2.58 (2H, t); 2.75 (1H, dd); 2.79 (2H, t); 3.22 (1H, bs); 6.48 (1H, bs); 7.21 (1H, bs); 7.32 (1H, bs).

EXAMPLE 49

3β-(2-(1-Pyrrolidinyl)ethylthio)-17β-(3-furyl)-5β-androstan-14β-ol (I-bw)

The title compound (I-bw) (0.18 g) was obtained as a pale yellow solid from 3β-mercapto-17β(3-furyl)-5β-androstan-14β-ol (II-d, Prep. 3)(0.30 g) using the same procedure described in Ex. 47.

$^1$H-NMR (300 MHz, CDCl$_3$, ppm from TMS): 0.72 (3H, s); 0.95 (3H, s); 2.50-2.60 (4H, m); 2.60-2.70 (4H, m); 2.75 (1H, dd); 3.26 (1H, bs); 6.48 (1H, bs); 7.21 (1H, bs); 7.32 (1H, bs).

EXAMPLE 50

3β-(3-(1-Piperazinyl)propylthio)-17β-(3-furyl)-5,β)-androstan-14β-ol dioxalate(I-bx)

The title compound (I-by) (0.33 g) was obtained as a pale yellow solid from 3β-mercapto-17β-(3-furyl)-5β-androstan-14β-ol (II-d, Prep. 3)(0.30 g) using the same procedure described in Ex. 47.

$^1$H-NMR (300 MHz, CDCl$_3$, ppm from TMS): 0.72 (3H, s); 0.95 (3H, s); 2.42 (6H, bt); 2.52 (2H, t); 2.75 (1H, dd); 2.90 (4H, t); 3.24 (1H, bs); 6.48 (1H, bs); 7.21 (1H, bs); 7.32 (1H, bs).

EXAMPLE 51

3β-(2-(2-(1-Pyrrolidinyl)ethoxy)ethylthio)-17β-(3-furyl)-5β-androstan-14β-ol (I-by)

To a solution of 1.5 g of 3β-mercapto-17β-(3-furyl)-5β-androstan-14β-ol (II-d, Prep. 3) in 20 ml of dimethylformamide, where nitrogen was continuously bubbled in, 1.0 ml of 2-bromoethanol and 0.18 g of sodium hydride (60% dispersion in mineral oil) were added at room temperature. The reaction mixture was stirred for 7 hrs, then diluted with water and extracted with ethyl acetate. The organic solution was washed with water, dried over sodium sulfate and evaporated to dryness under reduced pressure. The crude product was purified by flash-chromatography (SiO$_2$) using n-exane/ethyl acetate 60/40 as eluant, affording 1.2 g of 3β-(2-hydroxyethylthio)-17β-(3-furyl)-5β-androstan-14β-ol as a colourless oil.

$^1$H-NMR (300 MHz, CDCl$_3$, ppm from TMS): 0.70 (3H, s); 0.90 (3H, s); 2.72 (2H, t); 2.74 (1H, dd); 3.22 (1H, bs); 3.70 (2H, t); 6.44 (1H, bs); 7.18 (1H, bs); 7.30 (1H, bs).

To a solution of 0.90 g of 3β-(2-hydroxyethylthio)-17β-(3-furyl)-5β-androstan-14β-ol, in 9 ml of dry pyridine, 0.64 g of tosylchloride were added. After 5 hrs 10 ml of water and 50 ml of ethyl acetate were added. The organic phase was washed with water, dried over anhydrous sodium sulfate to give 1.2 g of 3β-(2-tosyioxyethylthio)-17β-(3-furyl)-5β-androstan-14β-ol as a colourless oil.

$^1$H-NMR (300 MHz, CDCl$_3$, ppm from TMS): 0.63 (3H, s); 0.90 (3H, s); 2.48 (3H, s); 2.74 (1H, dd); 3.02–3.15 (2H, m); 4.15–4.20 (2H, m); 6.46 (1H, bs); 7.20 (1H, bs); 7.28–7.40 (5H, m).

To a solution of 0.21 g of 1-(2-hydroxyethyl)pyrrolidine in 5 ml of dimethylformamide, 0.076 g of NaH (60% dispersion in mineral oil) were added and the mixture was kept at reflux for 2 hrs, then 0.35 g of 3β-(2-tosyloxyethylthio)-17β-(3-furyl)-5β-androstan-14β-ol in 2 ml of dimethylformamide was added, the mixture was kept at reflux temperature for 4 hrs and 5 ml of water were added. The residue was extracted with methylene chloride, the organic layer was washed with water to neutral pH, dried over anhydrous sodium sulfate and evaporated to dryness under reduced pressure. The crude product was purified by flash-chromatography (SiO$_2$) using methylene chloride/methanol 95/5 as eluant to give 0.22 g of the title compound (I-bz) as a white pasty solid.

$^1$H-NMR (300 MHz, CDCl$_3$, ppm from TMS): 0.70 (3H, s); 0.90 (3H, s); 1.72–1.82 (4H, m); 2.50–2.60 (6H, m); 2.67–2.75 (3H, m); 3.55–3.65 (4H, m); 6.44 (1H, bs); 7.18 (1H, bs); 7.30 (1H, bs).

EXAMPLE 52

3β-(2-(N-(2-(1-Pyrrolidinyl)ethyl)methylamino)ethylthio)-17β-(3-furyl)-5β-androstan-14β-ol (I-bz)

To a solution of 0.34 g of N-(2-(1-pyrrolidinyl)ethyl) methylamine in 5 ml of dimethylformamide, 0.045 g of NaH (60% dispersion in mineral oil) were added under nitrogen and the mixture was stirred at room temperature for half an hr; a solution of 0.50 g of 3β-(2-tosyloxyethylthio)-17β-(3-furyl)-5β-androstan-14β-ol, prepared as described in Ex. 51, in 2 ml of dimethylformamide was added, the mixture was stirred for another 4 hrs and then 7 ml of water were poured in. The residue was extracted with ethyl acetate, the organic solution was washed with water to neutral pH, dried over anhydrous sodium sulfate and evaporated to dryness under reduced pressure. The crude product was purified by flash-chromatography (SiO$_2$) using methylene chloride/methanol 95/5 as eluant to give 0.28 g of the title compound (I-ca) as an amorphous solid.

$^1$H-NMR (300 MHz, CDCl$_3$, ppm from TMS): 0.70 (3H, s); 0.90 (3H, s); 1.72–1.92 (4H, m); 2.50–2.60 (6H, m); 2.70–2.80 (3H, m); 3.50–3.65 (4H, m); 6.44 (1H, bs); 7.18 (1H, bs); 7.30 (1H, bs).

EXAMPLE 53

3β-(3-Dimethylaminopropylthio)-17β-(3-furyl)-5β-Androstan-14β-ol oxalate (I-ca)

The title compound (I-ca) (0.16 g) was obtained as a pale yellow solid from 3β-mercapto-17β-(3-furyl)-5β-androstan-14β-ol (II-d, Prep. 3)(0.20 g) using the same procedure described in Ex. 47.

$^1$H-NMR (300 MHz, CDCl$_3$, ppm from TMS): 0.72 (3H, s); 0.95 (3H, s); 2.22 (9H, s); 2.36 (2H, t); 2.52 (2H, t); 2.73 (1H, dd); 3.22 (1H, bs); 6.48 (1H, bs); 7.21 (1H, bs); 7.32 (1H, bs).

EXAMPLE 54

3β-(3-Aminopropylthio)-14β-methoxy-17β-(3-furyl)-5β-androstane oxalate (I-cb)

The title compound (I-cb) (0.11 g) was obtained as a white solid from 3β-mercapto-14β-methoxy-17β-(3-furyl)-5β-androstane (prepared starting from 14β-methoxy-17β-(3-furyl)-5β-androstan-3β-ol (II-c, Prep. 2)according to the sequence described in Prep. 1, Prep. 4 and Prep. 6) (0.23 g) using the same procedure described in Ex. 47.

1H-NMR (300 MHz, CD$_3$OD, ppm from TMS): 0.77 (3H, s); 0.96 (3H, s); 2.61 (2H, m); 3.31 (3H, s); 3.40 (1H, m); 6.35 (1H, bs); 7.19 (1H, bs); 7.33 (1H, bs).

EXAMPLE 55

3β-(2-(1-Pyrrolidinyl)ethylthio)-14β-methoxy-17β-(3-furyl)-5β-androstan oxalate (I-cc)

The title compound (I-cc) (0.19 g) was obtained as a pale yellow solid from 0.25 g of 3β-mercapto-14β-methoxy-17β-(3-furyl)-5β-androstane (prepared starting from 14β-methoxy-17β-(3-furyl)-5β-androstan-3β-ol (II-c, Prep. 2) according to the sequence described in Prep. 1, Prep. 4 and Prep. 6) using the same procedure described in Ex. 47.

$^1$H-NMR (300 MHz, CD3OD, ppm from TMS): 0.78 (3H, s); 0.98 (3H, s); 2.60 (2H, m); 3.31 (3H, s); 3.40 (1H, m); 6.37 (1H, bs); 7.19 (1H, bs); 7.32 (1H, bs).

EXAMPLE 56

3β-(3-Aminoprgpylthio)-17β-(3-furyl)-androst-4-en-14β-ol oxalate (I-cd)

The title compound (I-cd) (0.15 g) was obtained as a white solid from 0.20 g of 3β-mercapto-17β-(3-furyl)-androst-4-en-14β-ol (prepared starting from 17β-(3-furyl)-androst-4-ene-3β,14β-diol, prepared as described in Ex. 20, according to the sequence described in Prep. 1, Prep. 4 and Prep. 6) using the same procedure described in Ex. 47.

$^1$H-NMR (300 MHz, CD3OD, ppm from TMS): 0.72 (3H, s); 1.08 (3H, s); 3.19 (1H, m); 5.30 (1H, s); 6.45 (1H, bs); 7.23 (1H, bs); 7.33 (1H, bs).

EXAMPLE 57

3β-(2-(1-Pyrrolidinyl)ethylthio)-17β-(3-furyl)-androst-4-en-14β-ol oxalate (I-ce)

The title compound (I-ce)(0.18 g) was obtained as a white solid from 0.22 g of 3β-mercapto-17β-(3-furyl)-androst-4-en-14β-ol (prepared starting from 17β-(3-furyl)-androst-4-ene-3β,14β-diol, prepared as described in Ex. 20, according to the sequence described in Prep.

1, Prep. 4 and Prep. 6) using the same procedure described in Ex. 47.

$^1$H-NMR (300 MHz, CD3OD, ppm from TMS): 0.70 (3H, s); 1.08 (3H, s); 3.19 (1H, m); 5.30 (1H, s); 6.46 (1H, bs); 7.20 (1H, bs); 7.31 (1H, bs).

EXAMPLE 58

3β-(3-Aminopropylthio)-17β-(3-furyl)-androst-5-en-14β-ol oxalate (I-cf)

The title compound (I-cf) (0.15 g) was obtained as a pale yellow pasty solid from 0.30 g of 3β-mercapto-17β-(3-furyl)-androst-5-en-14β-ol (prepared starting from 17β-(3-furyl)-androst-5-ene-3β,14β-diol, prepared as described in Ex. 22, according to the sequence described in Prep. 1, Prep. 4 and Prep. 6) using the same procedure described in Ex. 47.

$^1$H-NMR (300 MHz, CDCl$_3$, ppm from TMS): 0.72 (3H, s); 1.01 (3H, s); 2.63 (2H, bt); 3.23 (2H, bs); 3.49 (1H, bm); 5.37 (1H, d); 6.47 (1H, bs); 7.23 (1H, bs); 7.31 (1H, bs).

EXAMPLE 59

3β-(2-(1-Pyrrolidinyl)ethylthio)-17β-(3-furyl)-androst-5-en-14β-ol oxalate (I-cg)

The title compound (I-cg) (0.17 g) was obtained as a pale yellow solid from 0.25 g of 3β-mercapto-17β-(3-furyl)-androst-5-en-14β-ol (prepared starting from 17β-(3-furyl)-androst-5-ene-3β,14β-diol, prepared as described in Ex. 22, according to the sequence described in Prep. 1, Prep. 4 and Prep. 6) using the same procedure described in Ex. 47.

$^1$H-NMR (300 MHz, CDCl$_3$, ppm from TMS): 0.71 (3H, s); 1.02 (3H, s); 2.63 (2H, bt); 3.49 (1H, bm); 5.39 (1H, d); 6.47 (1H, bs); 7.21 (1H, bs); 7.32 (1H, bs).

EXAMPLE 60

3β-(3-Aminopropylthio)-17β-(3-furyl)-5α-androstan-14β-ol oxalate (I-ch)

The title compound (I-ch) (0.18 g) was obtained as a white solid from 0.30 g of 3β-mercapto-17β-(3-furyl)-5α-androstan-14β-ol (prepared starting from 17β-(3-furyl)-5α-androstan-14β-ol, prepared as described in Ex. 24, according to the sequence described in Prep. 1, Prep. 4 and Prep. 6) using the same procedure described in Ex. 47.

$^1$H-NMR (300 MHz, CDCl$_3$, ppm from TMS): 0.70 (3H, s); 0.79 (3H, s); 2.90 (1H, m); 3.25 (3H, bs); 6.44 (1H, bs); 7.22 (1H, bs); 7.30 (1H, bs).

EXAMPLE 61

3β-(2-(1-Pyrrolidinyl)ethylthio)-17β-(3-furyl)-5α-androstan-14β-ol oxalate (I-Ci)

The title compound (I-ci) (0.15 g) was obtained as a pale brown solid from 0.25 g of 3β-mercapto-17β-(3-furyl)-5α-androstan-14β-ol (prepared starting from 17β-(3-furyl)-5α-androstan-14β-ol, prepared as described in Ex. 24, according to the sequence described in Prep. 1, Prep. 4 and Prep. 6) using the same procedure described in Ex. 47.

$^1$H-NMR (300 MHz, CDCl$_3$, ppm from TMS): 0.70 (3H, s); 0.79 (3H, s); 2.90 (1H, m); 6.44 (1H, bs); 7.22 (1H, bs); 7.30 (1H, bs).

EXAMPLE 62

3β-(3-Aminopropylthio)-14β,15β-epoxy-17β-(3-furyl)-5β-androstane oxalate (I-cj)

The title compound (I-cj) (0.22 g) was obtained as a white pasty solid from 14β,15β-epoxy-17β-(3-furyl)-5β-androstane-3β-thiol (II-e, Prep. 4), (0.30 g) using the same procedure described in Ex. 47.

$^1$H-NMR (300 MHz, CDCl$_3$, ppm from TMS): 0.75 (3H, s); 0.98 (3H, s); 2.28 (1H, m); 2.65 (3H, bs); 3.30 (3H, bs); 3.47 (1H, s); 6.47 (1H, bs); 7.17 (1H, bs); 7.27 (1H, bs).

EXAMPLE 63

3β-(2-(1-Pyrrolidinyl)ethylthio)-14β,15β-epoxy-17β-(3-furyl)-5β-androstane oxalate (I-ck)

The title compound (I-ck) (0.24 g) was obtained as a white solid from 14β,15β-epoxy-17β-(3-furyl)-5β-androstane-3β-thiol (II-e, Prep.4)(0.35 g) using the same procedure described in Ex. 47.

$^1$H-NMR (300 MHz, CDCl$_3$, ppm from TMS): 0.75 (3H, s); 0.98 (3H, s); 2.70 (3H, m); 3.20 (3H, m); 3.48 (1H, s); 6.41 (lit, bs); 7.18 (1H, bs); 7.28 (1H, bs).

EXAMPLE 64

3β-(3-Aminopropylthio), 14β,15β-epoxy-17β-(3-furyl)-androst-4-ene oxalate (I-cl)

The title compound (I-cl) (0.19 g) was obtained as a white solid from 0.26 g of 14β,15β-epoxy-17β-(3-furyl)-androst-4-ene-3β-thiol (prepared starting from 14β,15β-epoxy-17β-(3-furyl)-androst-4-en-3β-ol, prepared as described in Ex. 28, according to the sequence described in Prep. 1, Prep. 4 and Prep. 6) using the same procedure described in Ex. 47.

$^1$H-NMR (300 MHz, CD3OD, ppm from TMS): 0.76 (3H, s); 1.02 (3H, s); 2.66–2.71 (3H, m); 3.20 (1H, m); 3.41 (2H, bs); 3.59 (1H, s); 5.28 (1H, s); 6.40 (1H, bs); 7.17 (1H, bs); 7.29 (1H, bs).

EXAMPLE 65

3β-(2-(1-Pyrrolidinyl)ethylthio)-14β,15β-epoxy-17β-(3-furyl)-androst-4-ene oxalate (I-cm)

The title compound (I-cm) (0.21 g) was obtained as a pale brown solid from 0.25 g of 14β,15β-epoxy-17β-(3-furyl)-androst-4-ene-3β-thiol (prepared starting from 14β,15β-epoxy-17β-(3-furyl)-androst-4-en-3β-ol, prepared as described in Ex. 28, according to the sequence described in Prep. 1, Prep. 4 and Prep. 6) using the same procedure described in Ex. 47.

$^1$H-NMR (300 MHz, CD3OD, ppm from TMS): 0.76 (3H, s); 1.01 (3H, s); 2.65–2.72 (3H, m); 3.20 (1H, m); 3.40 (2H, bs); 3.60 (1H, s); 5.28 (1H, s); 6.40 (1H, bs); 7.18 (1H, bs); 7.29 (1H, bs).

EXAMPLE 66

3β-(3-Aminopropylthio)-14β,15β-epoxy-17β-(3-furyl)-androst-5-ene oxalate (I-cn)

The title compound (I-cn) (0.20 g) was obtained as a pale yellow pasty solid from 0.25 g of 14β,15β-epoxy-17β-(3-furyl)-androst-5-ene-3β-thiol (prepared starting from 14β,15β-epoxy-17β-(3-furyl)-androst-5-en-3β-ol, prepared as described in Ex. 30, according to the sequence described in Prep. 1, Prep. 4 and Prep. 6) using the same procedure described in Ex. 47.

$^1$H-NMR (300 MHz, CD$_3$OD, ppm from TMS): 0.74 (3H, s); 1.01 (3H, s); 2.58 (2H, m); 2.72 (2H, d); 3.21 (2H, m); 3.47 (1H, m); 5.37 (1H, d); 6.39 (1H, bs); 7.18 (1H, bs); 7.30 (1H, bs).

EXAMPLE 67

3β-(2-(1-Pyrrolidinyl)ethylthio)- 14β,15β-epoxy-17β-3-furyl)-androst-5-ene oxalate (I,co)

The title compound (I-co) (0.28 g) was obtained as a white solid from 0.30 g of 14β,15β-epoxy-17β-(3-furyl)- androst-5-ene-3β-thiol (prepared starting from 14β,15β-epoxy-17β-(3-furyl)-androst-5-en-3β-ol (prepared as described in Ex. 30)according to the sequence described in Prep. 1, Prep. 4 and Prep. 6) using the same procedure described in Ex. 47.

¹H-NMR (300 MHz., CD₃OD, ppm from TMS): 0.76 (3H, s); 1.01 (3H, s); 2.60 (2H, m); 2.70 (2H, d); 3.22 (2H, m); 3.48 (1H, m); 5.40 (1H, d); 6.39 (1H, bs); 7.19 (1H, bs); 7.30 (1H, bs).

EXAMPLE 68

3β-(3-Aminopropylthio)-14,β,15β-epoxy-17β-(3-furyl)-5α-androstane oxalate (I,cp)

The title compound (I-ep) (0.23 g) was obtained as a white solid from 0.32 g of 14β,15β-epoxy-17β-(3-furyl)-5α-androstane- 3β-thiol (prepared starting from 14β,15β-epoxy-17β-(3-furyl)-5α-androstan-3β-ol, prepared as described in Ex. 32, according to the sequence described in Prep. 1, Prep. 4 and Prep. 6) using the same procedure described in Ex. 47.

¹H-NMR (300 MHz, CDCl₃, ppm from TMS): 0.74 (3H, s); 0.81 (3H, s); 2.87 (1H, m); 2.68 (3H, m); 3.19 (3H, m); 3.47 (1H, s); 6.39 (1H, bs); 7.16 (1H, bs); 7.28 (1H, bs).

EXAMPLE 69

3β-(2-(1-Pyrrolidinyl)ethylthio)-14β,15β-epoxy-17β-(3-furyl)-5α-androstane oxalate (I-cq)

The title compound (I-eq) (0.21 g) was obtained as a pale yellow amorphous solid from 0.25 g of 14β,15β-epoxy-17β-(3-furyl)-5α-androstane-3β-thiol (prepared starting from 14β,15β-epoxy-17β-(3-furyl)-5α-androstan-3β-ol, prepared as described in Ex. 32, according to the sequence described in Prep. 1, Prep. 4 and Prep. 6) using the same procedure described in Ex. 47.

¹H-NMR (300 MHz, CDCl₃, ppm from TMS): 0.73 (3H, s); 0.82 (3H, s); 2.90 (1H, m); 2.67 (3H, m); 3.20 (3H, m); 3.47 (1H, s); 6.39 (1H, bs); 7.18 (1H, bs); 7.26 (1H, bs).

EXAMPLE 70

3β-(3-Aminopropylthio)-17β-(3-furyl)-androst-4-ene oxalate (I-cr)

The title compound (I-cr) (0.18 g) was obtained as a white solid from 0.24 g of 17β-(3-furyl)-androst-4-ene-3β-thiol (prepared starting from 17β-(3-furyl)-androst-4-en-3β-ol, prepared as described in Ex. 37, according to the sequence described in Prep. 1, Prep. 4 and Prep. 6) using the same procedure described in Ex. 47.

¹H-NMR (300 MHz, CDCl₃, ppm from TMS): 0.50 (3H, s); 1.03 (3H, s); 2.64 (2H, bs); 3.16 (2H, m); 3.25 (2H, m); 5.29 (1H, s); 6.31 (1H, bs); 7.18 (1H, bs); 7.40 (1H, bs).

EXAMPLE 71

3β-(2-(1-Pyrrolidinyl)ethylthio)-17β-(3-furyl)-androst-4-ene, oxalate (I-cs)

The title compound (I-cs) (0.15 g) was obtained as a white solid from 0.20 g of 17β-(3-furyl)-androst-4-ene-3β-thiol (prepared starting from 17β-(3-furyl)-androst-4-en-3β-ol, prepared as described in Ex. 37, according to the sequence described in Prep. 1, Prep. 4 and Prep. 6) using the same procedure described in Ex. 47.

¹H-NMR (300 MHz, CDCl₃, ppm from TMS): 0.51 (3H, s); 1.02 (3H, s); 2.64 (2H, bs); 3.16 (2H, m); 3.25 (2H, m); 5.30 (1H, s); 6.30 (1H, bs); 7.18 (1H, bs); 7.42 (1H, bs).

EXAMPLE 72

3β-(3-Aminopropylthio)-17β-(3-furyl)-androst-5-ene oxalate (I-ct)

The title compound (I-ct) (0.24 g) was obtained as a pale yellow solid from 0.27 g of 17β-(3-furyl)-androst-5-ene-3β-thiol (prepared starting from 17β-(3-furyl)-androst-5-en-3β-ol, prepared as described in Ex. 39, according to the sequence described in Prep. 1, Prep. 4 and Prep. 6) using the same procedure described in Ex. 47.

¹H-NMR (300 MHz, CDCl₃, ppm from TMS): 0.53 (3H, s); 0.98 (3H, s); 2.68 (2H, m); 3.20 (2H, m); 3.46 (1H, m); 6.28 (1H, bs); 7.21 (1H, bs); 7.35 (1H, bs).

EXAMPLE 73

3β-(2-(1-Pyrrolidinyl)ethylthio)-17β-(3-furyl)-androst-5-ene oxalate (I-cu)

The title compound (I-cu) (0.10-g) was obtained as a white solid from 0.10 g of 17β-(3-furyl)-androst-5-ene-3β-thiol (prepared starting from 17β-(3-furyl)-androst-5-en-3β-ol, prepared as described in Ex. 39, according to the sequence described in Prep. 1, Prep. 4 and Prep. 6) using the same procedure described in Ex. 47.

¹H-NMR (300 MHz, CDCl₃, ppm from TMS): 0.52 (3H, s); 0.97 (3H, s); 2.68 (2H, m); 3.22 (2H, m); 3.45 (1H, m); 6.28 (1H, bs); 7.21 (1H, bs); 7.34 (1H, bs).

EXAMPLE 74

3β-(3-Aminopropylthio)-17β-(3-furyl)-androstane oxalate (I-cv)

The title compound (I-cv) (0.12 g) was obtained as a white pasty solid from 0.26 g of 17β-(3-furyl)-androstane-3β-thiol (prepared starting from 17β-(3-furyl)-androstan-3β-ol, prepared as described in Ex. 41, according to the sequence described in Prep. 1, Prep. 4 and Prep. 6) using the same procedure described in Ex. 47.

¹H-NMR (300 MHz, CDCl₃, ppm from TMS): 0.51 (3H, s); 0.73 (3H, s); 2.65 (2H, bs); 3.710 (1H, m); 3.28 (2H, m); 6.29 (1H, bs); 7.20 (1H, bs); 7.36 (1H, bs).

EXAMPLE 75

3β-(2-(1-Pyrrolidinyl)ethylthio)-17β-(3-furyl)-androstane oxalate (I-cw)

The title compound (I-cw) (0.15 g) was obtained as a pale brown solid from 0.25 g of 17β-(3-furyl)-androstane-3β-thiol (prepared starting from 17β-(3-furyl)-androstan-3β-ol, prepared as described in Ex. 41, according to the sequence described in Prep. 1, Prep. 4 and Prep. 6) using the same procedure described in Ex. 47.

¹H-NMR (300 MHz, CDCl₃, ppm from TMS): 0.53 (3H, s); 0.71 (3H, s); 2.67 (2H, bs); 3.11 (1H, m); 3.26 (2H, m); 6.30 (1H, bs); 7.21 (1H, bs); 7.36 (1H, bs).

EXAMPLE 76

3β-(2-(3-Aminopropoxy)ethoxy)-17β-(3-furyl)-5β-androstan-14β-ol (I-cx)

The title compound (I-cx) (0.52 g) was obtained as a pale yellow solid from 2 g of 3β-(2-hydroxyethoxy)-17β-(3-furyl)-5β-andostran- 14β-ol, prepared as an intermediate in Ex.1, using the same procedure described in Ex. 2.

¹H-NMR (300 MHz, CDCl₃, ppm from TMS): 0.72 (3H, s); 0.92 (3H, s); 2.70–2.79 (3H, m); 3.49–3.62 (6H, m); 3.65 (1H, bs); 6.47 (1H, bs); 7.21 (1H, bs); 7.32 (1H, bs).

EXAMPLE 77

3β-(2-(3-Amino-2-hydroxypropoxy)ethoxy)-17β-(3, furyl)-5β-androstan-14β-ol (I-cy)

To a solution of 1.7 g of 3β-(2-(2,3-dihydroxypropoxy)ethoxy)-17β-(3-furyl)-5β-androstan-14β-ol, prepared from 3γ-(2-hydroxyethoxy)-17β-(3-furyl)-5β-andostran-14β-ol, prepared as an intermediate in Ex.1, according to the sequence described in Ex. 2 and Ex. 15, in 13 ml of dry pyridine, 0.80 g of tosyl chloride were added at a temperature of 0° C. After 5 hrs 60 ml of water and 250 ml of ethyl acetate were added, the organic layer was washed with water, dried over anhydrous sodium sulfate and evaporated to dryness under reduced pressure. The crude product was purified by flash-chromatography (SiO2)using n-hexane/ethyl acetate 70/30 as eluant to give 2 g of 3β-(2- (3-tosyloxy-2-hydroxypropoxy)ethoxy)-17β-(3-furyl)-5β-androstan-14β-ol as a white solid.

$^1$H NMR (300 MHz, CDCl$_3$, ppm from TMS): 0.72 (3H, s); 0.92 (3H, s); 2.45 (3H, s); 2.74 (1H, dd); 3.37–3.66 (7H, m); 3.91–4.00 (1H, m); 4.03–4.13 (2H, m); 6.47 (1H, bs); 7.20 (1H, bs); 7.30 (1H, bs); 7.35 (d, 2H); 7.82 (d, 2H).

To a solution of 2 g of 3β-(2-(3-tosyloxy-2-hydroxypropoxy)ethoxy)-17β-(3-furyl)-5β-androstan-14β-ol, in 15 ml of dimethylsulfoxide, 2.14 g of sodium azide were added at room temperature. The solution was kept at reflux for 3 hrs, then 30 ml of water were added and the residue was extracted with methylene chloride. The organic layer was washed with water, dried over anhydrous sodium sulfate and evaporated to dryness under reduced pressure. The crude product was purified by flash-chromatography (SiO2) using n-hexane/ethyl acetate 80/20 as eluant to give 1.4 g of 3β-(3-azido-2-hydroxypropoxy)-17β-(3-furyl)-5β-androstan-14β-ol.

$^1$H NMR (300 MHz, CDCl$_3$, ppm from TMS): 0.72 (3H, s); 0.92 (3H, s); 2.74 (1H, m); 3.37–3.66 (9H, m); 3.71–3.80 (1H, m); 6.47 (1H, bs); 7.21 (1H, bs); 7.32 (1H, bs).

A solution of 1 g of 3β-(3-azido-2-hydroxypropoxy)-17β-(3-furyl)-5β-androstan-14β-ol in 20 ml of diethyl ether is added to a suspension of 0.50 g of lithium aluminium hydride in 18 ml of diethyl ether. The mixture was kept at reflux for 12 hrs, then were added 0.5 ml of water, 0.5 ml of sodium hydroxyde (water solution 10%) and 1.9 ml of water. The mixture was filtered over a celite cake, the organic solution was washed with water, dried over sodium sulfate and evaporated to dryness under reduced pressure. The crude residue was purified by flash-chromatography (SiO2) using methylene chloride/methanol/30% ammonia solution 90/10/1 as eluant to give 0.65 g of the title compound (I-cy) as a light yellow solid.

$^1$H NMR (300 MHz, CDCl$_3$, ppm from TMS): 0.72 (3H, s); 0.92 (3H, s); 2.74 (1H, m); 3.37–3.66 (9H, m); 3.71–3.80 (1H, m); 6.47 (1H, bs); 7.22 (1H, bs); 7.32 (1H, bs).

EXAMPLE 78

3β-(2-(2,3-Diaminopropoxy)ethoxy)-17β-(3-furyl)-5β-androstan-14β-ol (I-cz)

The title compound (I-cz) (0.62 g) was obtained as a white solid from 1.5 g of 3β-(2-(2,3-ditosyloxypropoxy)ethoxy)-17β-(3-furyl)-5β-androstan-14β-ol prepared from 3β-(2-hydroxyethoxy)-17β(3-furyl)-5β-andostran-14β-ol, prepared as an intermediate in Ex.1, according to the sequence described in Ex. 2 and Ex. 15.

$^1$H-NMR (300 MHz, CDCl$_3$, ppm from TMS): 0.72 (3H, s); 0.92 (3H, s); 2.59–2.68 (1H, m); 2.71–2.86 (2H, m); 2.90–2.99 (1H, m); 3.37–3.67 (7H, m); 6.47 (1H, bs); 7.21 (1H, bs); 7.32 (1H, bs).

EXAMPLE 79

3β(2-(3-(1-Pyrrolidinyl)propoxy)ethoxy)-17 β-(3-furyl)-5β-androstan-14β-ol (I-da)

The title compound (I-da) (1.5 g) was obtained as a colourless oil from 3β-(2-tosyloxyethoxy)-17β-(3-furyl)-5β-androstan-14β-ol (2.1 g), prepared as described in Ex. 7, using the same procedure described in Ex. 8.

$^1$H-NMR (300 MHz, CDCl$_3$, ppm from TMS): 0.72 (3H, s); 0.92 (3H, s); 2.51–2.61 (4H, m); 2.62–2.68 (2H, m); 2.74 (1H, m); 3.49–3.62 (6H, m); 3.65 (1H, bs); 6.47 (1H, bs); 7.22 (1H, bs); 7.32 (1H, bs).

EXAMPLE 80

3β-(2-(3-(1-Pyrrolidinyl)propylamino)ethoxy)-17β-(3-furyl)-5β-androstan-14β-ol (I-db)

The title compound (I-db) (0.50 g) was obtained as a colourless oil from 3β-(2-tosyloxyethoxy)-17β-(3-furyl)-5β-androstan-14β5-ol (0.62 g), prepared as described in Ex. 7, using the same procedure described in Ex. 7.

$^1$H-NMR (300 MHz, CDCl$_3$, ppm from TMS): 0.72 (3H, s); 0.92 (3H, s); 2.51–2.61 (4H, m); 2.62–2.68 (2H, m); 2.71–2.85 (5H, m); 3.46–3.57 (2H, m); 3.63 (1H, bs); 6.47 (1H, bs); 7.22 (1H, bs); 7.32 (1H, bs).

PREPARATION OF INTERMEDIATES

Preparation 1

17β-(3-Furyl)-14β,15β-epoxy-5β-androstan-3α-ol (II-b)

To a solution of 5.0 g of 14β,15β-epoxy-17β-(3-furyl)-5β-androstan-3β-ol (E. Yoshii et al., Chem. Pharm. Bull., 1976, 24, 3216) in 70 ml of methylene chloride, 2.5 g of 4-methylmorpholine N-oxide, 0.25 g of tetrapropylammonium perruthenate and 4.0 g of powdered 4A molecular sieves were added at room temperature. After 4 hrs the solvent was evaporated to dryness under reduced pressure and the crude product purified by flash-chromatography (SiO2) using n-hexane/ethyl acetate 70/30 as eluant to give 7.9 g of 14β,15β-epoxy-17β-(3-furyl)-5β-androstan-3-one as a white solid.

$^1$H-NMR (300 MHz, CDCl$_3$, ppm from TMS): 0.76 (3H, s); 1.03 (3H, s); 2.65 (1H, d); 3.62 (1H, s); 6.50 (1H, bs); 7.18 (1H, bs); 7.29 (1H, bs).

To a solution of 4.5 g of 14β,15β-epoxy-17β-(3-furyl)-5β-androstan-3-one in 30 ml of dry tetrahydrofuran at-78° C, a solution of 9.8 g of tri-tert-butoxyaluminum-hydride in tetrahydrofuran was added dropwise. The mixture was stirred for 20 hrs, then 40 ml of water were added and the temperature raised to 25° C. The aluminum salts were filtered on a celite cake and washed with methanol. The solution was concentrated under reduced pressure and extracted with methylene chloride. The organic layer was dried over sodium sulfate and evaporated to dryness under reduced pressure to give 4.3 g of the title compound (II-b) as a white solid.

$^1$H-NMR (300 MHz, CDCl$_3$, ppm from TMS): 0.74 (3H, s); 1.00 (3H, s); 2.65 (1H, d); 3.51 (1H, s); 3.65 (1H, m); 6.48 (1H, bs); 7.18 (1H, bs); 7.29 (1H, bs).

Preparation 2

14β-Methoxy-17β-(3-furyl)-5β-androstan-3β-ol (II-c)

To a solution of 10 g of 17β-(3-furyl)-5β-androstane-3β,14β-diol (II-a: Ref. comp.) (Minato H. and Nagasaki T., *J. Chem. Soc.* (C), 1966, 377) in 80 ml of dimethylformamide, 18 g of imidazole and 20.0 g of t-butyldimethylsilyl chloride were added at 0° C. After 12 hrs the mixture was poured into water and extracted with ethyl acetate. The organic layer was dried over sodium sulfate and evaporated to dryness under reduced pressure and 15 g of crude 3β-tert-butyldimethylsilyloxy-17β-(3-furyl)-5β-androstan-14β-ol were obtained. A suspension of this protected alcohol and 1.3 g of KH in 75 ml of tetrahydrofuran was heated at 70° C. for an hr; then 2.7 g of methyl iodide were added. After 30' the mixture was poured into water and extracted with ethyl acetate. The organic layer was dried over sodium sulfate and evaporated to dryness under reduced pressure to give 12 g of 3β-tert-butyldimethylsilyloxy-14β-methoxy-17β-(3-furyl)-5β-androstane as a white amorphous solid.

$^1$H-NMR (300 MHz, CDCl$_3$, ppm from TMS): 0.080 (6H, s); 0.81 (3H, s); 0.93 (9H, s); 0.98 (3H, s); 2.13–2.30 (1H, m); 2.70 (1H, m); 3.38 (3H, s); 4.07 (1H, bs); 6.41 (1H, bs); 7.18 (1H, bs); 7.33 (1H, bs).

A solution of 3.0 g of 3β-tert-butyldimethylsilyloxy-14β-methoxy-17β-(3-furyl)-5β-androstane in 57 ml of a 1.0 M solution of tetrabutylammonium fluoride was heated at 70° C. under nitrogen for an hr and then poured into a saturated solution of sodium chloride. The mixture was extracted with ethyl acetate and the organic layer was dried over sodium sulfate, evaporated to dryness under reduced pressure and purified by flash-chromatography (SiO$_2$) using n-hexane/ethyl acetate 80/20 as eluant to give 2.0 g of the title compound (II-c) as a white solid.

$^1$H-NMR (300 MHz, CDCl$_3$, ppm from TMS): 0.78 (3H, s); 1.00 (3H, s); 2.15–2.30 (1H, m); 2.70 (1H, m); 3.40 (3H, s); 4.18 (1H, bs); 6.39 (1H, bs); 7.18 (1H, bs); 7.32 (1H, bs).

Preparation 3

3β-Mercapto-17β-(3-furyl)-5β-androstan-14β-ol (II-d)

To a solution of 1.5 g of 3β-acetylthio-17β-(3-furyl)-5β-androstan-14β-ol (VI-a, Prep. 5) in 20 ml of methanol, hydrogen was bubbled for 15', the solution was saturated with gaseous ammonia and kept on standing for 3 hrs at room temperature. The mixture was evaporated to dryness under reduced pressure and purified by flash-chromatography (SiO$_2$) using n-hexane/ethyl acetate 95/5 as eluant to give 1.2 g of the title compound (II-d) as a white solid.

$^1$H-NMR (300 MHz, CDCl$_3$, ppm from TMS): 0.72 (3H, s); 0.98 (3H, s); 2.17–2.31 (2H, m); 2.76 (1H, dd); 3.62 (1H, bs); 6.48 (1H, bs); 7.22 (1H, bs); 7.33 (1H, bs).

Preparation 4

14β,15β-Epoxy17β-(3-furyl)-5β-androstane-3β-thiol (II-e)

To a solution of 1.6 g of 3β-acetylthio-14β,15β-epoxy-17β-(3-furyl)-5β-androstane (VI-b, Prep. 6) in 20 ml of methanol, hydrogen was bubbled for 15', the solution was saturated with gaseous ammonia and kept on standing for 3 hrs at room temperature. The mixture was evaporated to dryness under reduced pressure and purified by flash-chromatography (SiO$_2$) using n-hexane/ethyl acetate 95/5 as eluant to give 1.3 g of the title compound (II-e) as a white solid.

$^1$H-NMR (300 MHz, CDCl$_3$, ppm from TMS): 0.76 (3H, s); 1.02 (3H, s); 2.65 (1H, d); 3.51 (1H, s); 3.63 (1H, bs); 6.48 (1H, bs); 7.18 (1H, bs); 7.29 (1H, bs).

Preparation 5

3β-Acetylthio-17β-(3-furyl)-5β-androstan-14β-ol (VI-a)

Diisopropyl azodicarboxylate (3.6 ml) was added to a solution of 4.7 g of triphenylphosphine in 90 ml of tetrahydrofuran at 0° C. and the mixture was stirred for 30'. To this mixture a solution of 2.2 g of 17β-(3-furyl)-5β-androstane-3α,14β-diol (Humber D. and al., *Steroids*, 1983, 42, 189) and 2.2 ml of thiolacetic acid in 90 ml of tetrahydrofuran was added dropwise and the residue was stirred for an hr at room temperature. The solvent was evaporated to dryness under reduced pressure and the crude product was purified by flash-chromatography (SiO$_2$) using n-hexane/ethyl acetate 95/5 as chant to give 1.6 g of the title compound (VI-a) as a white solid.

$^1$H-NMR (300 MHz, CDCl$_3$, ppm from TMS): 0.72 (3H, s); 0.96 (3H, s); 2.31 (3H, s); 2.77 (1H, dd); 4.08 (1H, bs); 6.48 (1H, bs); 7.21 (1H, bs); 7.32 (1H, bs).

Preparation 6

3β-Acetylthio-14β,15β-epoxy-17β-(3-furyl)-5β-androstane (VI,b)

Diisopropyl azodicarboxylate (3.5 ml) was added to a solution of 4.5 g of triphenylphosphine in 85 ml of tetrahydrofuran at 0° C. and the mixture was stirred for 30'. To this mixture a solution of 2.0 g of 14β,15β-epoxy-17β-(3-furyl)-5β-androstan-3α-ol and 2.05 ml of thiolacetic acid in 90 ml of tetrahydrofuran was added dropwise and the resulting mixture was stirred for an hr at room temperature. The solvent was evaporated to dryness under reduced pressure and the crude product was purified by flash-chromatography (SiO$_2$) using n-hexane/ethyl acetate 95/5 as eluant to give 1.7 g of the title compound (VI-b) as a white solid.

$^1$H-NMR (300 MHz, CDCl$_3$, ppm from TMS): 0.73 (3H, s); 1.00 (3H, s); 2.32 (3H, s); 2.65 (1H, d); 3.50 (1H, s); 4.10 (1H, bs); 6.48 (1H, bs); 7.18 (1H, bs); 7.29 (1H, bs).

We claim:

1. Cyclopentanperhydrophenanthren-17β-(3-furyl)-3-derivatives of formula (I)

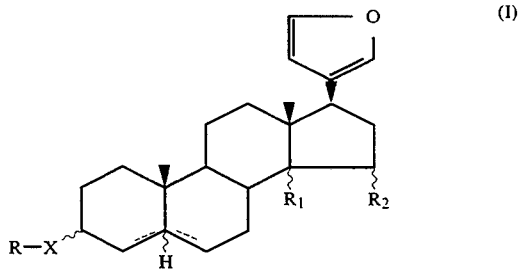

wherein:

X is O or S;

the symbol ∼ means that the substituents in positions 3, 5, 14, and 15 can have an α or β configuration, with the proviso that when X=S only the 3β configuration is present;

the symbol ≡ means that single or double bonds can be present;

R is C2–C6 alkyl or C3–C6 alkenyl, substituted independently by a quaternary ammonium group or one or more OR3, SR3, NR4R5, C(NH)NR6R7, with the proviso that when X is oxygen and R1 is βOH and R2 is H and the configuration in position 5 is β and C2–C6 alkyl is ethyl or n-propyl, NR4R5 is not dimethylamino;

R1 is H or hydroxy or methoxy or O(CH2)$_n$NR8R9; wherein n is 2 or 3;

R2 is H;

R3 is C2–C4 alkyl substituted by one or more NR6R7 or by NR6R7 and OH;

R4, R5 are independently H, methyl, C2–C6 alkyl or C3–C6 alkenyl unsubstituted or substituted or by one or more NR6R7, or NR6R7 and OH, or R4 is hydrogen and R5 is C(NH)NH2;

R6, R7 are independently H, C1–C4 alkyl;

R8, R9 are independently H, methyl, ethyl and the pharmaceutically acceptable salts thereof.

2. A compound according to claim 1, which is selected from:

3β-(2-Trimethylammonium-ethoxy)-17β-(3-furyl)-5β-androstan-14β-ol chloride
3β-(2-Aminoethoxy)-17β-(3-furyl)-5β-androstan-14β-ol
3β-(3-Aminopropoxy)-17β-(3-furyl)-5β-androstan-14β-ol
3β-(4-Aminobutoxy)-17β-(3-furyl)-5β-androstan-14β-ol
3β-(4-Aminobut-(2-en)oxy)-17β-(3-furyl)-5β-androstan-14β-ol
3β-(4-Aminobut-(2-yn)oxy)-17β-(3-furyl)-5β-androstan-14β-ol
3β-(2-Methylaminoethoxy)-17β-(3-furyl)-5β-androstan-14β-ol
3β-(2-(2-Amidino)ethoxy)-17β-(3-furyl)-5β-androstan-14β-ol
3β-(2-(2-Aminoethoxy)ethoxy)-17β-(3-furyl)-5β-androstan-14β-ol
3β-(2-(3-Aminopropoxy)ethoxy)-17β-(3-furyl)-5β-androstan-14β-ol
3β-(2-(3-Dimethylaminopropoxy)ethoxy)-17β-(3-furyl)-5β-androstan-14β-ol
3β(2-(3-Dimethylaminopropylthio)ethoxy)-17α-(3-furyl)-5β-androstan-14β-ol
3β-(2-(3-Dimethylaminopropylamino)ethoxy)-17β-(3-furyl)-5β-androstan-14β-ol
3β-(2-(3-Amino-2-hydroxypropoxy)ethoxy)-17β-(3-furyl)-5β-androstan-14β-ol
3β-(2-(2,3-Diaminopropoxy)ethoxy)-17β-(3-furyl)-5β-androstan-14β-ol
3β-(2-Guanidinoethoxy)-17β-(3-furyl)-5β-androstan-14β-ol
3β-(3-Guanidinopropoxy)-17β-(3-furyl)-5β-androstan-14β-ol
3β-(4-Guanidinobutoxy)-17β-(3-furyl)-5β-androstan-14β-ol
3β-(2,3-Diaminopropoxy)-17β-(3-furyl)-5β-androstan-14β-ol
3β-(3-(3-Amino-2-hydroxypropoxy)propoxy)-17β-(3-furyl)-5β-androstan-14β-ol
3β-(3-(3-Amino-2-hydroxypropylamino)propoxy)-17β-(3-furyl)-5β-androstan-14β-ol
3β-(3-Aminopropoxy)-14β-methoxy-17β-(3-furyl)-5β-androstane
3β-(3-Aminopropoxy)-17β-(3-furyl)-androst-4-en-14β-ol
3β-(3-Aminopropoxy)-17β-(3-furyl)-androst-5-en-14β-ol
3β-(3-Aminopropoxy)-17β-(3-furyl)-5α-androstan-14β-ol
3β-(3-Aminopropoxy)-17β-(3-furyl)-5β-androstan-14α-ol
3β-(3-Aminopropoxy)-14β,15β-epoxy-17β-(3-furyl)-5β-androstane
3β-(3-Aminopropoxy)-14β,15β-epoxy-17β-(3-furyl)-androst-4-ene
3β-(3-Aminopropoxy)-14β,15β-epoxy-17β-(3-furyl)-androst-5-ene
3β-(3-Aminopropoxy)-14β,15β-epoxy-17β-(3-furyl)-5α-androstane
3β-(3-Aminopropoxy)-14α,15α-epoxy-17β-(3-furyl)-5β-androstane
3β-(3-Aminopropoxy)-17β-(3-furyl)-5β,14β-androstane
3β-(3-Aminopropoxy)-17β-(3-furyl)-androst-4-ene
3β-(3-Aminopropoxy)-17β-(3-furyl)-androst-5-ene
3β-(3-Aminopropoxy)-17β-(3-furyl)-5α-androstane
3β-(3-Aminopropoxy)-17β-(3-furyl)-5α-androstane and the corresponding X=S derivatives and for X=O the corresponding 3α derivatives.

3. A pharmaceutical composition for treatment of cardiovascular disorder or hypertension containing a compound of formula (I) of claim 1 or a pharmaceutically acceptable salt thereof and a pharmaceutically acceptable carrier and/or diluent.

4. A method for the treatment of a patient having cardiovascular disorder or hypertension, which comprises administering to the patient an effective amount of a compound of formula (I) of claim 1, or pharmaceutically acceptable salt thereof.

5. The method of claim 4 for the treatment of hypertension.

6. The method of claim 4 for the treatment of cardiac failure.

* * * * *